(12) United States Patent
Chen

(10) Patent No.: US 6,875,769 B2
(45) Date of Patent: Apr. 5, 2005

(54) SUBSTITUTED 6,6-HETERO-BICYCLIC DERIVATIVES

(75) Inventor: Yuhpyng L. Chen, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/336,884

(22) Filed: Jan. 6, 2003

(65) Prior Publication Data

US 2003/0114671 A1 Jun. 19, 2003

Related U.S. Application Data

(63) Continuation of application No. 09/242,777, filed on Dec. 15, 1999, now abandoned, which is a continuation of application No. PCT/IB97/00904, filed on Jul. 21, 1997.

(51) Int. Cl.⁷ .................. A61K 31/47; A61K 31/4709; C07D 215/12; C07D 403/04
(52) U.S. Cl. .............. 514/256; 514/311; 514/312; 514/313; 514/314; 544/333; 546/152; 546/153; 546/159; 546/162; 546/167; 546/168; 546/173
(58) Field of Search .................. 546/152, 168, 546/173, 153, 159, 162, 167; 544/333; 514/256, 311, 312, 313, 314

(56) References Cited

U.S. PATENT DOCUMENTS 4,343,804 A * 8/1982 Munson, Jr. et al. ....... 546/159
6,482,836 B1 * 11/2002 Huang et al. ............... 514/313

OTHER PUBLICATIONS

Wommack et al., Chemical Abstracts, vol. 76:94453, 1972.*
Huang et al., Chemical Abstracts, vol. 129:330738, 1998.*

* cited by examiner

*Primary Examiner*—Richard L. Raymond
(74) *Attorney, Agent, or Firm*—Ladas & Parry LLP

(57) ABSTRACT

This invention relates to compounds of the formula

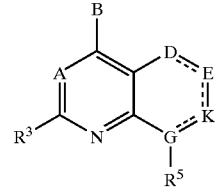

I wherein A, B, D, E, K, G, $R^3$ and $R^5$ are defined as in the specification, and to the pharmaceutically acceptable salts of such compounds.

33 Claims, No Drawings

SUBSTITUTED 6,6-HETERO-BICYCLIC DERIVATIVES

The present application is a continuation of U.S. Ser. No. 09/242,777, filed Dec. 15, 1999 (now abandoned) which is a continuation of PCT/IB97/00904, filed on Jul. 21, 1997 which claims the benefit of U.S. Provisional Patent Application No. 60/124,659, filed Aug. 27, 1996.

BACKGROUND OF THE INVENTION

This invention relates to certain pharmaceutically active substituted 6,6-hetero-bicyclic derivatives, pharmaceutical compositions containing them and methods of administering them to subjects in need of their corticotropin releasing factor antagonist activity.

The substituted heterocyclic derivatives claimed in this case exhibit activity as corticotropin releasing factor (hormone) CRF (CRH) antagonists.

CRF antagonists are mentioned in U.S. Pat. Nos. 4,605,642 and 5,063,245 referring to peptides and pyrazolinones, respectively. They are also referred to in the following: PCT Patent Application PCT/IB95/00439 (corresponding U.S. application issued as U.S. Pat. No. 5,962,479), which designates the United States and was filed on Jun. 6, 1995 and published on Dec. 14, 1995; PCT Patent Application PCT/IB95/00373 (corresponding U.S. application issued as U.S. Pat. No. 6,248,753), which designates the United States and was filed on May 18, 1995 and published on Dec. 21, 1995; U.S. patent application Ser. No. 08/448,539 (pending in U.S.), which was filed in the PCT on Nov. 12, 1993 and entered the U.S. national phase on Jun. 14, 1995; PCT Patent Application WO 95/10506 (corresponding U.S. application issued as U.S. Pat. No. 6,107,301), which was filed on Oct. 12, 1993 and published on Apr. 20, 1995, and U.S. patent application Ser. No. 08/481,413 (corresponding U.S. application issued as U.S. Pat. No. 6,218,397), which was filed in the PCT on Nov. 26, 1993 and entered the U.S. national phase on Jul. 24, 1995; U.S. patent application Ser. No. 08/254,820 (corresponding U.S. application issued as U.S. Pat. No. 5,705,646), which was filed on Apr. 19, 1995; Provisional U.S. Patent Application No. 60/008,396, which was filed on Dec. 8, 1995; and Provisional U.S. Patent Application No. 60/006,333 (corresponding U.S. application issued as U.S. Pat. No. 6,403,599), which was filed on Nov. 8, 1995. All the foregoing patent applications are incorporated herein by reference in their entireties.

The importance of CRF antagonists is set out in the literature, e.g., P. Black, *Scientific American SCIENCE & MEDICINE*, 1995, p. 16–25; T. Lovenberg, et al., *Current Pharmaceutical Design*, 1995, 1, 305–316; and, U.S. Pat. No. 5,063,245, which is referred to above. A recent outline of the different activities possessed by CRF antagonists is found in M. J. Owens et al., *Pharm. Rev.*, Vol. 43, pages 425 to 473 (1991), also incorporated herein by reference. Based on the research described in these two and other references, CRF antagonists are effective in the treatment of a wide range of stress-related illnesses, mood disorders such as depression, major depressive disorder, single episode depression, recurrent depression, child abuse induced depression, postpartum depression, dysthemia, bipolar disorders and cyclothymia; chronic fatigue syndrome; eating disorders such as anorexia and bulimia nervosa; generalized anxiety disorder; panic disorder; phobias; obsessive-compulsive disorder, post-traumatic stress disorder, pain perception such as fibromyalgia; headache; gastrointestinal diseases; hemorrhagic stress; ulcers; stress-induced psychotic episodes; fever; diarrhea; post-operative ileus, colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiarrhetic hormone; obesity; chemical dependencies and addictions; drug and alcohol withdrawal symptoms; infertility, cancer; infertility; muscular spasms; urinary incontinence; hypoglycemia and immune dysfunctions including stress induced immune dysfunctions, immune suppression and human immunodeficiency virus infections; and stress-induced infections in humans and animals.

The compounds of this invention are also believed to be inhibitors of CRH binding protein and therefore useful in the treatment of disorders the treatment of which can be effected or facilitated by inhibiting such protein. Examples of such disorders are Alheimer's disease and obesity.

SUMMARY OF THE INVENTION

The present invention relates to compounds of the formula

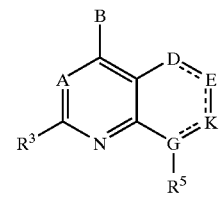

I the dashed lines represent optional double bonds;

A is nitrogen or $CR^7$;

B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$;

G is nitrogen or $CR^4$ and is single bonded to all atoms to which it is attached, or G is carbon and is double bonded to K;

K is nitrogen or $CR^6$ when double bonded to G or E, or K is oxygen, sulfur, C=O, C=S, $CR^6R^{12}$ or $NR^8$ when single bonded to both adjacent ring atoms, or K is a two atom spacer, wherein one of the two ring atoms of the spacer is oxygen, nitrogen, sulfur, C=O, C=S, $CR^6R^{12}$, $NR^6$ or $CR^6$, and the other is $CR^6R^{12}$ or $CR^9$;

D and E are each, independently, C=O, C=S, sulfur, oxygen, $CR^4R^6$ or $NR^8$ when single bonded to both adjacent ring atoms, or nitrogen or $CR^4$ when it is double bonded to an adjacent ring atom;

the 6- or 7-membered ring that contains D, E, K and G may contain from one to three double bonds, from zero to two heteroatoms selected from oxygen, nitrogen and sulfur, and from zero to two C=O or C=S groups, wherein the carbon atoms of such groups are part of the ring and the oxygen and sulfur atoms are substituents on the ring;

$R^1$ is $C_1-C_6$ alkyl optionally substituted with from one or two substituents independently selected from hydroxy, fluoro, chloro, bromo, iodo, $C_1$–$C_4$ alkoxy, $CF_3$, —C(=O)($C_1$–$C_4$alkyl), —C(=O)—O—($C_1$–$C_4$)alkyl, —OC(=O)($C_1$–$C_4$ alkyl), —OC(=O)N($C_1$–$C_4$ alkyl)($C_1$–$C_2$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —S($C_1$–$C_4$ alkyl), —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or ($C_1$–$C_4$ alkylene) aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl may optionally and independently be replaced by an oxygen or sulfur atom or by NZ wherein Z is hydrogen, $C_1$–$C_4$ alkyl or benzyl, and wherein each of the foregoing $R^2$ groups may optionally be substituted with from one to three substituents independently selected from chloro, fluoro, hydroxy and $C_1$–$C_4$ alkyl, or with one substituent selected from $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_{16}$alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl);

—NR$^1$R$^2$ or CR$^1$R$^2$R$^{10}$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by NZ$^2$ wherein Z$^2$ is hydrogen, benzyl or $C_1$–$C_4$ alkyl;

$R^3$ is hydrogen, $C_1$–$C_4$ alkyl, —O($C_1$–$C_4$ alkyl), chloro, fluoro, bromo, iodo, —S($C_1$–$C_4$ alkyl) or —SO$_2$($C_1$–$C_4$ alkyl);

each $R^8$, $R^9$ and $R^{12}$ is selected, independently, from hydrogen and $C_1$–$C_2$ alkyl;

each $R^4$ and $R^6$ that is attached to a carbon atom is selected, independently, from hydrogen, $C_1$–$C_6$ alkyl, fluoro, chloro, bromo, iodo, hydroxy, hydroxy ($C_1$–$C_2$ alkyl), trifluoromethyl, cyano, amino, nitro, —O($C_1$–$C_4$ alkyl), —N($C_1$–$C_4$ alkyl)($C_1$–$C_2$ alkyl), —CH$_2$SCH$_3$, —S($C_1$–$C_4$ alkyl), —CO($C_1$–$C_4$ alkyl), —C(=O)H or —C(=O)O ($C_1$–$C_4$ alkyl), wherein each of the $C_1$–$C_2$ alkyl moieties in the foregoing $R^4$ and $R^6$ groups may optionally contain one double or triple bond; and $R^6$, when attached to a nitrogen atom, is selected from hydrogen and ($C_1$–$C_4$)alkyl;

$R^5$ is substituted phenyl, naphthyl, pyridyl or pyrimidyl, wherein each of the foregoing $R^5$ groups is substituted with from two to four substituents $R^{13}$, wherein up to three of said substituents may be selected, independently, from chloro, $C_1$–$C_6$ alkyl, —O($C_1$–$C_6$ alkyl) and —($C_1$–$C_6$ alkylene)O ($C_1$–$C_6$ alkyl), and wherein one of said substituents may be selected, independently, from bromo, iodo, formyl, cyano, trifluoromethyl, nitro, amino, —NH($C_1$–$C_4$ alkyl), —N($C_1$–$C_2$ alkyl)($C_1$–$C_6$ alkyl), —C(=O)O($C_1$–$C_4$ alkyl), —C(=O)($C_1$–$C_4$ alkyl), —COOH, —SO$_2$NH($C_1$–$C_4$ alkyl), —SO$_2$N($C_1$–$C_2$ alkyl)($C_1$–$C_4$ alkyl), —SO$_2$NH$_2$, —NHSO$_2$($C_1$–$C_4$ alkyl), —(CO—$C_1$alkylene)-S—($C_1$–$C_2$alkyl), —($C_0$–$C_1$alkylene)-SO—($C_1$–$C_2$alkyl), —($C_0$-$C_1$alkylene)-SO$_2$—($C_1$-$C_2$alkyl) and ($C_1$–$C_4$alkylene)-OH, and wherein each of the $C_1$–$C_4$ alkyl and $C_1$–$C_6$ alkyl moieties in the foregoing $R^5$ groups may optionally be substituted with one or two substituents independently selected from fluoro, hydroxy, amino, methylamino, dimethylamino and acetyl;

$R^7$ is hydrogen, methyl, halo (e.g., chloro, fluoro, iodo or bromo), hydroxy, methoxy, —C(=O)($C_1$–$C_2$ alkyl), —C(=O)O($C_1$–$C_2$ alkyl), hydroxymethyl, trifluoromethyl or formyl;

$R^{10}$ is hydrogen, hydroxy, methoxy or fluoro; and $R^{11}$ is hydrogen or $C_1$–$C_4$ alkyl;

with the proviso that in the ring containing D, E, K and G of formula I, there can not be two double bonds adjacent to each other;

and the pharmaceutically acceptable salts of such compounds.

Examples of more specific embodiments of formula I are the following, wherein X is oxygen, sulfur or NR$^8$, wherein R$^8$ is defined as above, each dashed line represents an optional double bond and (R)$_n$ represents from zero to four substitutents, wherein such substitutents are as defined above in the definition of formula I.

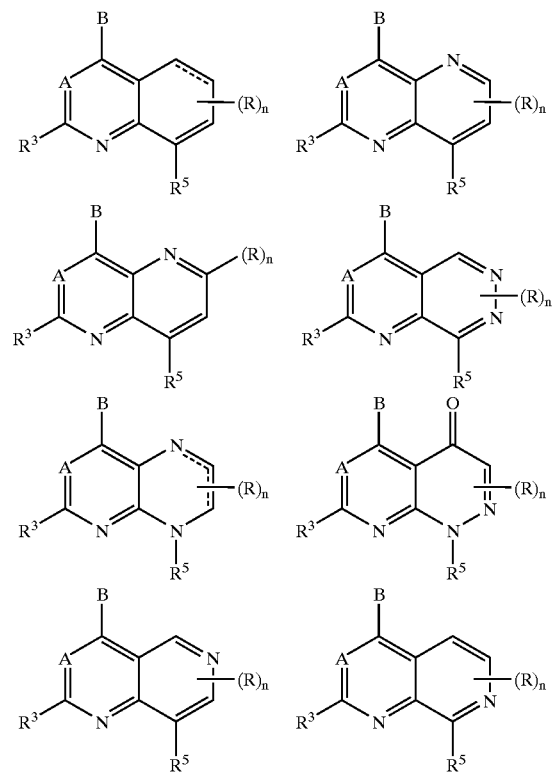

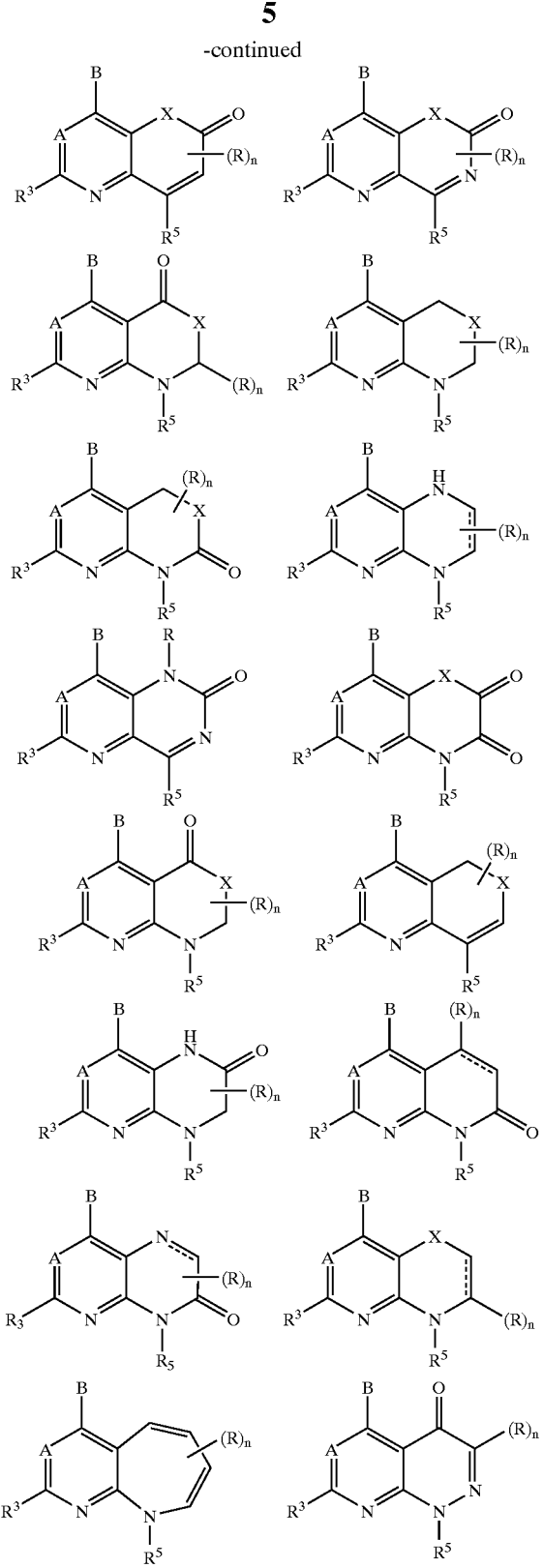

More specific embodiments of the invention include compounds of the formula I wherein B is —CHR$^1$R$^2$, —NR$^1$R$^2$, —NHCHR$^1$R$^2$, —OCHR$^1$R$^2$, or —SCHR$^1$R$^2$, and R$^1$ is C$_1$–C$_6$ alkyl, which may optionally be substituted with one hydroxy, fluoro, CF$_3$ or C$_1$–C$_4$ alkoxy group and may optionally contain one double or triple bond; and R$^2$ is benzyl or C$_1$–C$_6$ alkyl, which may optionally contain one double or triple bond, wherein said C$_1$–C$_6$ alkyl and the phenyl moiety of said benzyl may optionally be substituted with one fluoro, hydroxy, CF$_3$, C$_1$–C$_2$ alkyl, C$_1$–C$_2$ alkoxy or chloro group.

Other more specific embodiments of this invention include compounds of the formula I wherein B is or contains an NR$^1$R$^2$ or CR$^1$R$^2$R$^{10}$ moiety which forms a saturated or unsaturated 5-membered carbocyclic ring wherein one of the ring carbon atoms may optionally be replaced by an oxygen or sulfur atom.

Other more specific embodiments of the invention include compounds of formula I wherein R$^3$ is methyl, ethyl, chloro or methoxy; each of R$^4$, R$^6$, R$^8$, R$^9$, and R$^{12}$ is, independently, hydrogen or methyl; and R$^5$ is di- or tri-substituted phenyl, pyridyl, or pyrimidyl, wherein up to three of the substitutents can be selected, independently, from C$_1$–C$_4$ alkyl, —O—(C$_1$–C$_4$ alkyl) and —(C$_1$–C$_4$ alkylene)-O—(C$_1$–C$_4$ alkyl), and wherein one of the substituents can be selected, independently, from —(C$_0$–C$_1$alkylene)-S—(C$_1$–C$_2$alkyl), —(C$_0$–C$_1$alkylene)-SO—(C$_1$–C$_2$alkyl), —(C$_0$–C$_1$alkylene)-SO$_2$—(C$_1$–C$_2$alkyl),CF$_3$, —OCF$_3$, —CHO, —(C$_1$–C$_4$ alkylene)-OH, cyano, chloro, fluoro, bromo and iodo, and wherein each of the forgoing (C$_1$–C$_4$) alkyl groups may optionally contain one double or triple bond.

Other more specific embodiments of the invention include compounds of the formula I wherein A is N, CH or CCH$_3$.

Other more specific embodiments of the invention include compounds of the formula I wherein G is N.

Other more specific embodiments of the invention include compounds of the formula I wherein G is carbon and the ring containing D, E, K and G is a benzo ring.

Other more specific embodiments of the invention include compounds of the formula I wherein G is N; D is NH or N(methyl); and E≕K is CH$_2$—CH$_2$, CH═CH, C(O)—CH$_2$ or CH$_2$—C(O).

Other more specific embodiments of the invention include compounds of the formula I wherein G is N and D≕E≕K is C(O)—O—CH$_2$, CH$_2$—O—CH$_2$, C(O)—CH$_2$—CH$_2$, C(O)—CH═CH, CH$_2$—CH$_2$—CH$_2$—, CH$_2$—CH$_2$—C(O), CH═CH—C(O), CH═CH—CH$_2$, CH═CH—NH or CH═CH—NCH$_3$.

Examples of preferred compounds of the invention are:

4-(butyl-ethyl-amino)-2,6-dimethyl-8-(2,4,6-trimethyl-phenyl)-5,8-dihydro-6H-pyrido[2,3-d]pyrimidin-7-one;

8-(1-ethyl-propoxy)-6-methyl-4-(2,4,6-trimethyl-phenyl)-3,4-dihydro-1H-pyrido[2,3-b]pyrazin-2-one;

8-(1-ethyl-propoxy)-6-methyl-4-(2,4,6-trimethyl-phenyl)-1,2,3,4-tetrahydro-pyrido[2,3-b]pyrazine;

4-(1-ethyl-propoxy)-2-methyl-8-(2,4,6-trimethyl-phenyl)-quinoline;

5-(1-ethylpropoxy)-7-methyl-1-(2,4,6-trimethyl-phenyl)-1,4-dihydro-2H-3-oxa-1,8-diaza-naphthalene;

5-(1-ethyl-propoxy)-7-methyl-1-(2,4,6-trimethyl-phenyl)-1,2-dihydro-3-oxa-1,8-diaza-naphthalen-4-one;

8-(1-ethyl-propoxy)-1,6-dimethyl-4-(2,4,6-trimethyl-phenyl)-1,2,3,4-tetrahydro-pyrido[2,3-b]pyrazine;

(1-ethyl-propyl)-[2-methyl-8-(2,4,6-trimethyl-phenyl)-quinolin-4-yl]-amine;

Other examples of compounds of the formula I are the following:

4-(butyl-ethyl-amino)-2,6-dimethyl-8-(2,6-dimethyl-4-bromo-phenyl)-5,8-dihydro-6H-pyrido[2,3-d]pyrimidin-7-one;

4-(butyl-ethyl-amino)-2-methyl-8-(2,6-dimethyl-4-bromo-phenyl)5,8-dihydro-6H-pyrido[2,3-d]pyrimidin-7-one;

4-(1-ethyl-propoxy)-2-methyl-8-(2,6-dimethyl-4-bromo-phenyl)-5,8-dihydro-6H-pyrido[2,3-d]pyrimidin-7-one;

(butyl-ethyl)-[2-methyl-8-(2,6-dimethyl-4-bromo-phenyl)-5,6,7,8-tetrahydro-pyrido[2,3-d]pyrimidin-4-yl]-amine;

(propyl-ethyl)-[2-methyl-8-(2,6-dimethyl-4-bromo-phenyl)-5,6,7,8-tetrahydro-pyrido[2,3-d]pyrimidin-4-yl]-amine;

(diethyl)-[2-methyl-8-(2,6-dimethyl-4-bromo-phenyl)-5,6,7,8-tetrahydro-pyrido[2,3-d]pyrimidin-4-yl]-amine;

(1-ethyl-propyl)-[2-methyl-8-(2,6-dimethyl-4-bromo-phenyl)-5,6,7,8-tetrahydro-pyrido[2,3-d]pyrimidin-4-yl]-amine;

(1-ethyl-propoxy)-2-methyl-8-(2,6-dimethyl-4-bromo-phenyl)-5,6,7,8-tetrahydro-pyrido[2,3-d]pyrimidine;

4-(butyl-ethyl-amino)-2-methyl-8-(2,4,6-trimethyl-phenyl)-5,8-dihydro-6H-pyrido[2,3-d]pyrimidin-7-one;

4-(1-ethyl-propoxy)-2-meth-8-(2,4,6-trimethyl-phenyl)-5,8-dihydro-6H-pyrido[2,3-d]pyrimidin-7-one;

(butyl-ethyl)-[2-methyl-8-(2,4,6-trimethyl-phenyl)-5,6,7,8-tetrahydro-pyrido[2,3-d]pyrimidin-4-yl]-amine;

(propyl-ethyl)-[2-methyl-8-(2,4,6-trimethyl-phenyl)-5,6,7,8-tetrahydro-pyrido[2,3-d]pyrimidin-4-yl]-amine;

(diethyl)-[2-methyl-8-(2,4,6-trimethyl-phenyl)-5,6,7,8-tetrahydro-pyrido[2,3-d]pyrimidin-4-yl]-amine;

(1-ethyl-propyl)-[2-methyl-8-(2,4,6-trimethyl-phenyl)-5,6,7,8-tetrahydro-pyrido[2,3-d]pyrimidin-4-yl]-amine;

(1-ethyl-propoxy)-2-methyl-8-(2,4,6-trimethyl-phenyl)-5,6,7,8-tetrahydro-pyrido[2,3-d]pyrimidine;

8-(1-ethyl-propoxy)-6-methyl-4-(2,6-dimethyl-4-bromo-phenyl)-3,4-dihydro-1H-pyrido[2,3-b]pyrazin-2-one;

8-(1-ethyl-propoxy)-6-methyl-4-(2,6-dimethyl-4-bromo-phenyl)-1,2,3,4-tetrahydro-pyrido[2,3-b]pyrazine;

4-(1-ethyl-propoxy)-2-methyl-8-(2,6-dimethyl-4-bromo-phenyl)-quinoline;

5-(1-ethyl-propoxy)-7-methyl-1-(2,6-dimethyl-4-bromo-phenyl)-1,4-dihydro-2H-3-oxa-1,8-diaza-naphthalene;

5-(1-ethyl-propoxy)-7-methyl-1-(2,6-dimethyl-4-bromo-phenyl)-1,2-dihydro-3-oxa-1,8-diaza-naphthalen-4-one;

8-(1-ethyl-propoxy)-1,6-dimethyl-4-(2,6-dimethyl-4-bromo-phenyl)-1,2,3,4-tetrahydro-pyrido[2,3-b]pyrazine;

(1-ethyl-propyl)-[2-methyl-8-(2,6-dimethyl-4-bromo-phenyl)-quinolin-4-yl]-amine;

4-(butyl-ethyl-amino)-2,6-dimethyl-8-(2,6-dimethyl-4-chloro-phenyl)-5,8-dihydro-6H-pyrido[2,3-d]pyrimidin-7-one;

8-(1-ethyl-propoxy)-6-methyl-4-(2,6-dimethyl-4-chloro-phenyl)-3,4-dihydro-1H-pyrido[2,3-b]pyrazin-2-one;

8-(1-ethyl-propoxy)-6-methyl-4-(2,6-dimethyl-4-chloro-phenyl)-1,2,3,4-tetrahydro-pyrido[2,3-b]pyrazine;

4-(1-ethyl-propoxy)-2-methyl-8-(2,6-dimethyl-4-chloro-phenyl)-quinoline;

5-(1-ethyl-propoxy)-7-methyl-1-(2,6-dimethyl-4-chloro-phenyl)-1,4-dihydro-2H-3-oxa-1,8-diaza-naphthalene;

5-(1-ethyl-propoxy)-7-methyl-1-(2,6-dimethyl-4-chloro-phenyl)-1,2-dihydro-3-oxa-1,8-diaza-naphthalen-4-one;

8-(1-ethyl-propoxy)-1,6-dimethyl-4-(2,6-dimethyl-4-chloro-phenyl)-1,2,3,4-tetrahydro-pyrido[2,3-b]pyrazine;

(1-ethyl-propyl)-[2-methyl-8-(2,6-dimethyl-4-chloro-phenyl)-quinolin-4-yl]-amine;

8-(1-hydroxymethyl-propoxy)-6-methyl-4-(2,4,6-trimethyl-phenyl)-3,4-dihydro-1H-pyrido[2,3-b]pyrazin-2-one;

8-(1-hydroxymethyl-propylamino)-6-methyl-4-(2,4,6-trimethyl-phenyl)-3,4-dihydro-1H-pyrido[2,3-b]pyrazin-2-one;

8-(1-ethyl-propylamino)-6-methyl-4-(2,4,6-trimethyl-phenyl)-3,4-dihydro-1H-pyrido[2,3-b]pyrazin-2-one;

8-diethylamino-6-methyl-4-(2,4,6-trimethyl-phenyl)-3,4-dihydro-1H-pyrido[2,3-b]pyrazin-2-one;

8-(ethyl-propyl-amino)-6-methyl-4-(2,4,6-trimethyl-phenyl)-3,4-dihydro-1H-pyrido[2,3-b]pyrazin-2-one;

8-(butyl-ethyl-amino)-6-methyl-4-(2,4,6-trimethyl-phenyl)-3,4-dihydro-1H-pyrido[2,3-b]pyrazin-2-one;

8-(1-hydroxymethyl-propoxy)-6-methyl-4-(2,4,6-trimethyl-phenyl)-1,2,3,4-tetrahydro-pyrido[2,3-b]pyrazine;

8-(1-hydroxymethyl-propylamino)-6-methyl-4-(2,4,6-trimethyl-phenyl)-1,2,3,4-tetrahydro-pyrido[2,3-b]pyrazine;

8-(1-ethyl-propylamino)-6-methyl-4-(2,4,6-trimethyl-phenyl)-1,2,3,4-tetrahydro-pyrido[2,3-b]pyrazine;

8-diethylamino-6-methyl-4-(2,4,6-trimethyl-phenyl)-1,2,3,4-tetrahydro-pyrido[2,3-b]pyrazine;

8-(ethyl-propyl-amino)-6-methyl-4-(2,4,6-trimethyl-phenyl)-1,2,3,4-tetrahydro-pyrido[2,3-b]pyrazine;

8-(butyl-ethyl-amino)-6-methyl-4-(2,4,6-trimethyl-phenyl)-1,2,3,4-tetrahydro-pyrido[2,3-b]pyrazine;

4-(1-hydroxymethyl-propoxy)-2-methyl-8-(2,4,6-trimethyl-phenyl)-quinoline;

4-(1-hydroxymethyl-propylamino)-2-methyl-8-(2,4,6-trimethyl-phenyl)-quinoline;

4-(1-ethyl-propylamino)-2-methyl-8-(2,4,6-trimethyl-phenyl)-quinoline;

4-diethylamino-2-methyl-8-(2,4,6-trimethyl-phenyl)-quinoline;

4-(ethyl-propyl-amino)-2-methyl-8-(2,4,6-trimethyl-phenyl)-quinoline;

4-(butyl-ethyl-amino)-2-methyl-8-(2,4,6-trimethyl-phenyl)-quinoline;

5-(1-hydroxymethyl-propoxy)-7-methyl-1-(2,4,6-trimethyl-phenyl)-1,4-dihydro-2H-3-oxa-1,8-diaza-naphthalene;

5-(1-hydroxymethyl-propylamino)-7-methyl-1-(2,4,6-trimethyl-phenyl)-1,4-dihydro-2H-3-oxa-1,8-diaza-naphthalene;

5-(1-ethyl-propylamino)-7-methyl-1-(2,4,6-trimethyl-phenyl)-1,4-dihydro-2H-3-oxa-1,8-diaza-naphthalene;

5-diethylamino-5-methyl-1-(2,4,6-trimethyl-phenyl)-1,4-dihydro-2H-3-oxa-1,8-diaza-naphthalene;

5-(ethyl-propyl-amino)-7-methyl-1-(2,4,6-trimethyl-phenyl)-1,4-dihydro-2H-3-oxa-1,8-diaza-naphthalene; and 8-(butyl-ethyl-amino)-6-methyl-4-(2,4,6-trimethyl-phenyl)-1,4-dihydro-2H-3-oxa-1,8-diaza-naphthalene.

The invention also relates to a pharmaceutical composition for the treatment, prevention or inhibition of (a) a disorder the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, nicotine, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; hypertension; tachycardia; congestive heart failure; osteoporosis; premature birth; and hypoglycemia in a mammal, including a human, comprising an amount of a compound of the formula I, or a pharmaceutically acceptable salt thereof, that is effective in the treatment of such disorder, and a pharmaceutically acceptable carrier.

The invention also relates to a method for the treatment, prevention or inhibition of (a) a disorder the treatment of which can be effected or facilitated by antagonizing CRF, including but not limited to disorders induced or facilitator by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stressdisorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome; Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, nicotine, cocaine, heroin, benzodiazepines, or other drugs); drug and alcohol withdrawal symptoms; hypertension; tachycardia; congestive heartfailure; osteoporosis; premature birth; and hypoglycemia in a mammal, including a human, comprising administering to a subject in need of said treatment an amount of a compound of the formula I, or a pharmaceutically acceptable salt thereof, that is effective in treating such disorder.

This invention also relates to a method of treating or preventing a disorder or condition, the treatment or prevention of which can be effected or facilitated by inhibiting CRH binding protein, in a mammal, including a human, comprising administering to said mammal a CRH binding protein inhibiting amount of a compound of the formula I, or a pharmaceutically acceptable salt thereof.

This invention also relates to a pharmaceutical composition for treating or preventing a disorder or conditon, the treatment or prevention of which can be effected or facilitated by inhibiting CRH binding protein in a mammal, including a human, comprising a CRH binding protein inhibiting amount of a compound of the formula I, or a pharmaceutically acceptable salt thereof, and a pharmaceutically acceptable carrier.

This invention includes all optical isomers and other stereoisomers of compounds of the formula I. When such compounds contain one or more chiral centers, it is understood that the invention includes the racemic mixtures as well as all individual enantiomers and diastereomers of such compounds, and mixtures thereof.

The compounds of this invention include compounds identical to those described above but for the fact that one or more hydrogen, nitrogen or carbon atoms are replaced by isotopes thereof (e.g., tritium or carbon-14 isotopes). Such compounds are useful as research and diagnostic tools in metabolism pharmokinetic studies and in binding assays.

DETAILED DESCRIPTION OF THE INVENTION

The following compounds having the formulas II through V are useful as intermediates in the synthesis of compounds of the formula I.

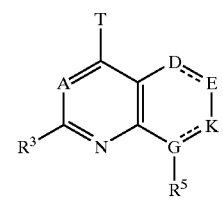

II

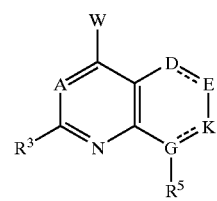

III

-continued

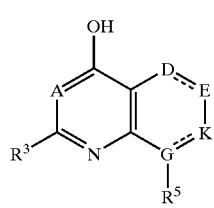
IV

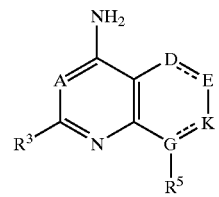
V

In the above compounds of formulas II–V, T is chloro, bromo, iodo or —OSO$_2$CF$_3$; W is cyano, —CHO, or —COO(C$_0$–C$_4$ alkyl), and A, D, E, K, G, R$^3$, and R$^5$ are as defined above with reference to formula I.

Methods of preparing the compounds and compositions of this invention are described below. In the discussion and reaction schemes that follow, R$^1$ through R$^{13}$, A, B, D, E, K, G, Z, Z$^2$, T and W, the dashed lines and structural formulas I, II, III, IV and V, unless otherwise indicated, are defined as above.

SCHEME 1

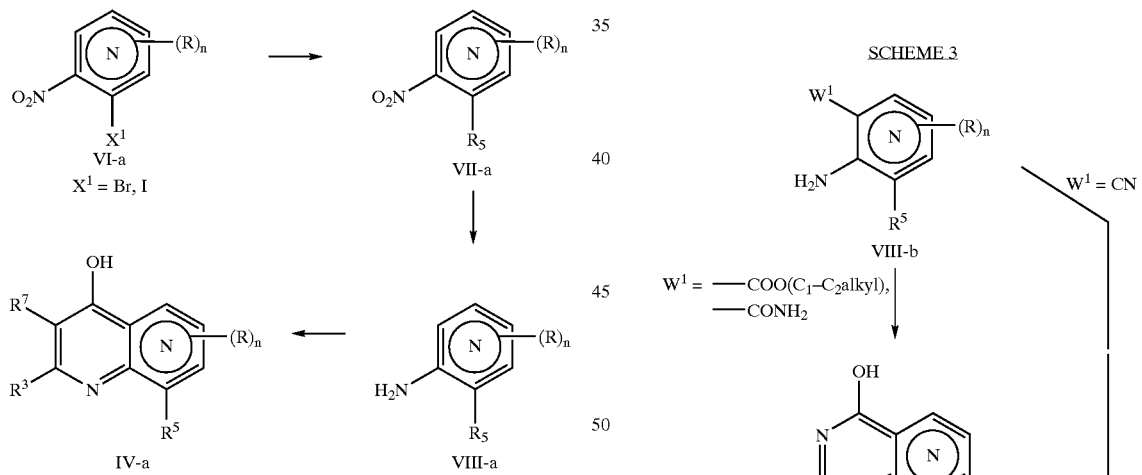

SCHEME 2

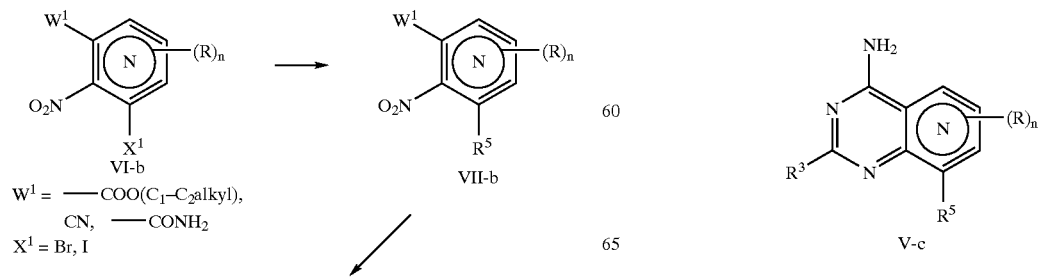

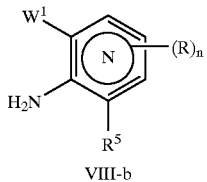
VIII-b

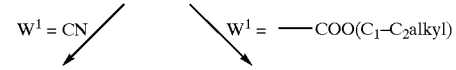

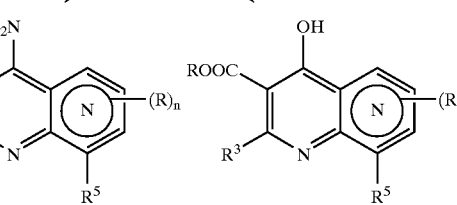
V-a
IV-b
R = C$_1$–C$_2$ alkyl

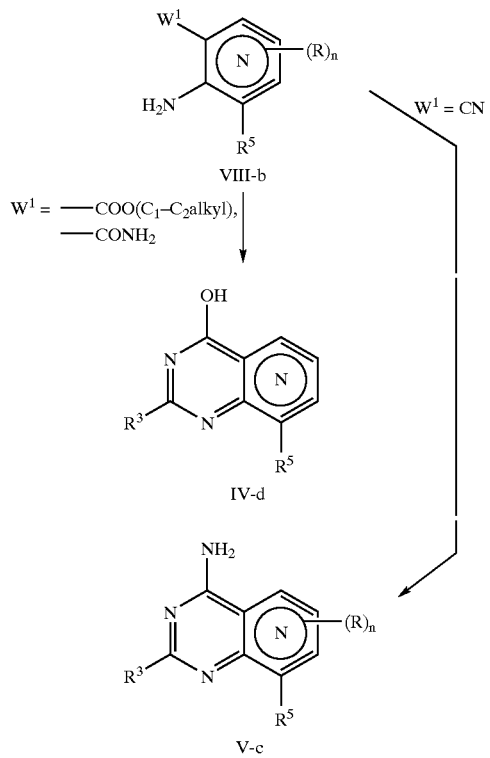

SCHEME 3

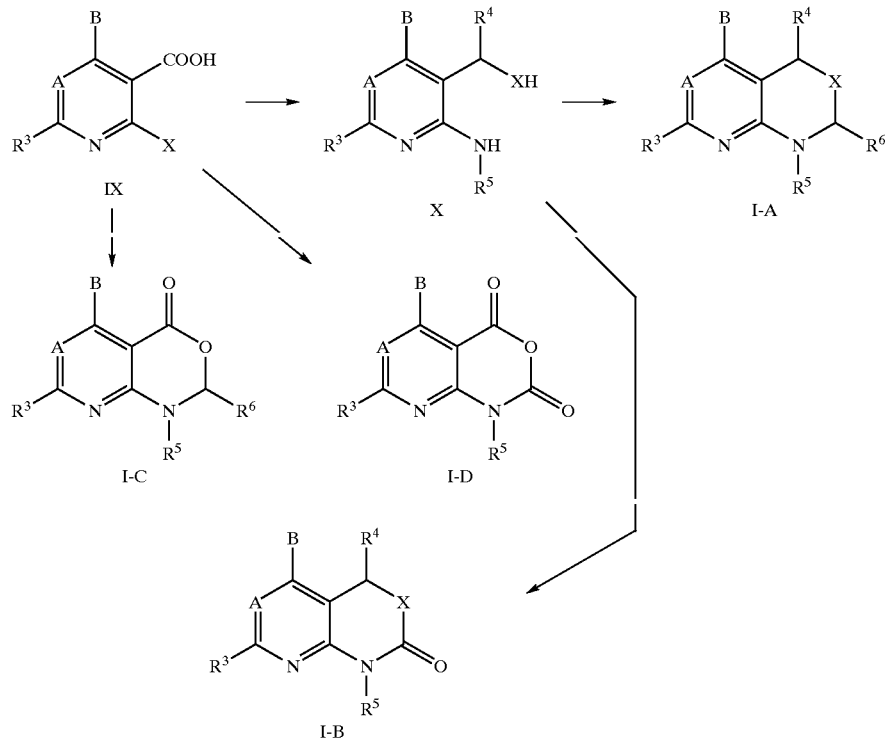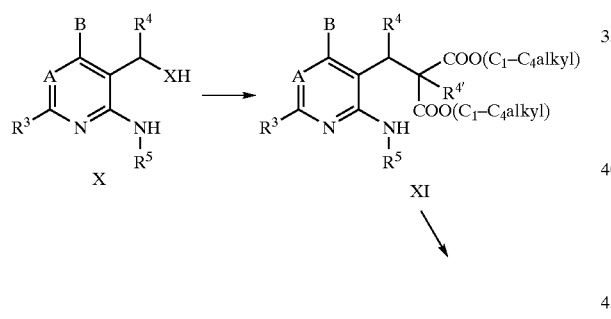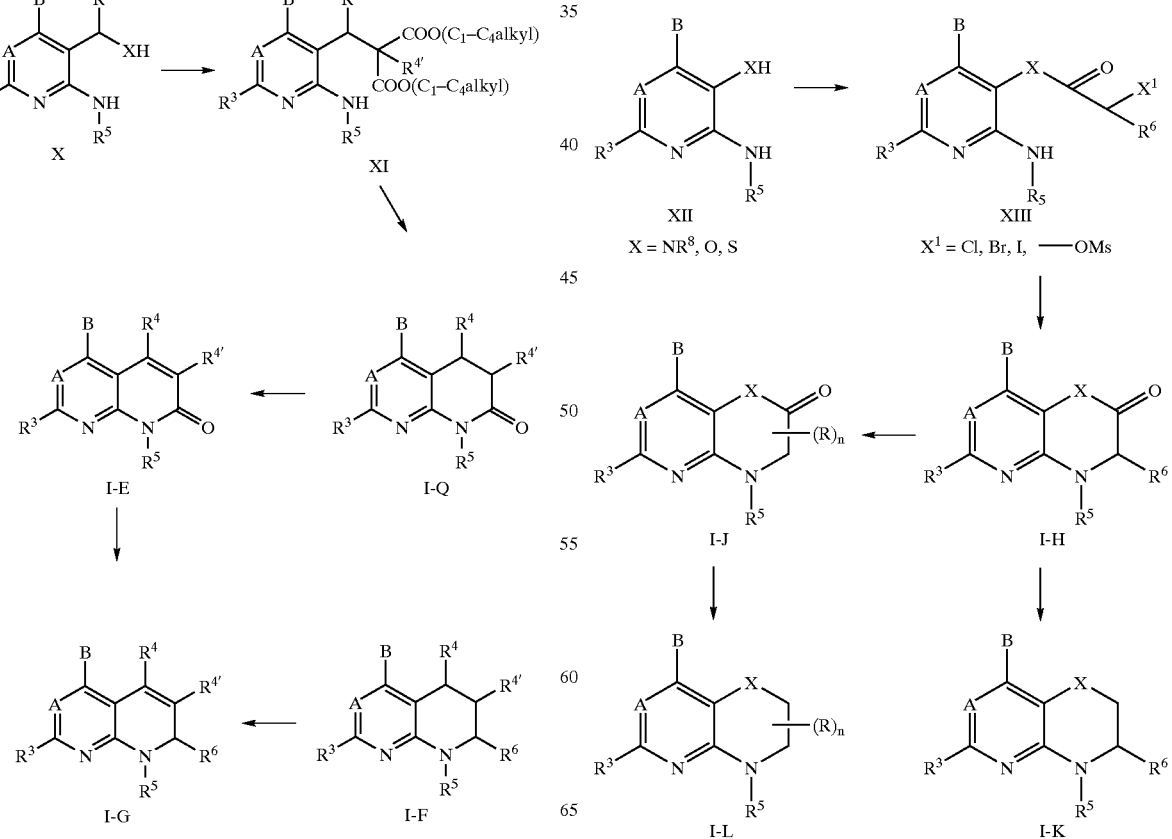

SCHEME 7

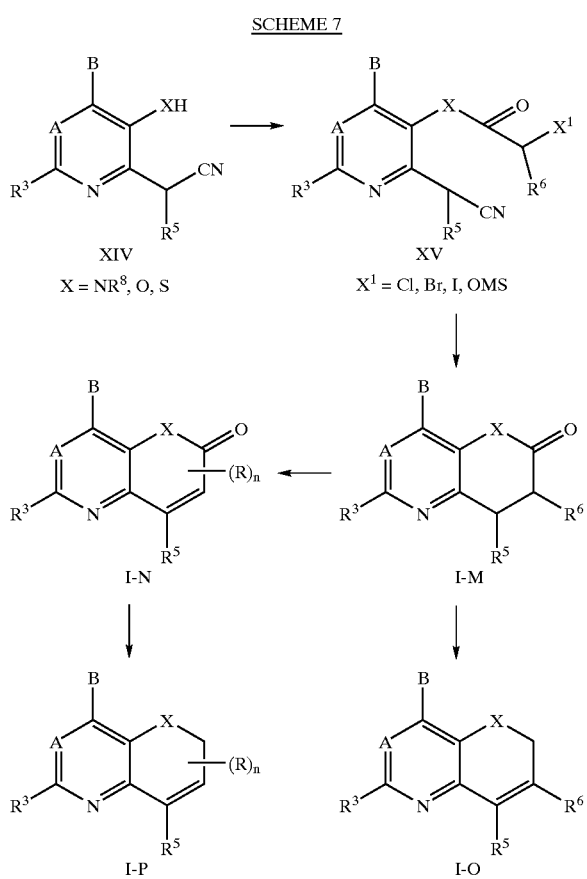

XIV
X = NR⁸, O, S

XV
X¹ = Cl, Br, I, OMS

I-N

I-M

I-P

I-O

Compounds of the formula I wherein B is —NR$^1$R$^2$ or —NHCR$^1$R$^2$R$^{11}$ may be prepared by reacting a compound of the formula II wherein T is chloro, bromo, or iodo with a compound of the formula BH, in the presence of a base, with or without an organometallic compound such as Cu(I) X, wherein X is chloro, bromo or iodo, or an acid (such as p-TsOH (Ts=Tosyl) or another sterically hindered phenol) or an equivalent agent known to those of skill in the art. Suitable solvents for this reaction include DMSO, NMP and THF. An excess of BH may be used as both the reagent and the base. Other bases such as potassium or sodium carbonate, a trialkylamine, a potassium or sodium ($C_1$–$C_4$ alkoxide) or sodium hydride may also be used. When R$^7$ is an electron withdrawing group such as —COO($C_1$–$C_4$alkyl) or CN, the reaction generally is carried out at a temperature between about room temperature and about 130° C. When R$^7$ is a non-electron withdrawing group, the reaction temperature can generally range from about 50° C. to about 270° C. and the pressure can generally range from about 4 psi to about 300 psi. A pressure reactor may be used.

Alternatively, the compounds of formula I may be prepared by reacting a compound of the formula II wherein T is bromo or iodo with 1 equivalent or an excess of BH and a base such as sodium or potassium carbonate or a sodium or potassium ($C_1$–$C_4$ alkoxide), in the presence of a palladium (II) or a palladium (0) catalyst such as Pd(OAc)$_2$ or Pd(PPh$_3$)$_4$, together with a racemic or chiral phosphino agent such as 2,2-bis(diphenylphosphino)-1,1-binaphthyl (BINAP). Alternatively, premade Pd(II)(BINAP) may be used directly in an appropriate inert (i.e., inert with respect to the reaction at hand) solvent such as toluene, xylene, or dioxane or sulfolane, at a temperature from about room temperature to about 180° C., preferably at about reflux temperature.

Compounds of the formula I wherein B is —OCR$^1$R$^2$R$^{11}$, —SCR$^1$R$^2$R$^{11}$, or —NHCR$^1$R$^2$R$^{11}$ may be prepared by reacting compounds in the formula II wherein T is chloro, bromo or iodo with a compound of the formula BH in the presence of a base which is capable of deprotonation of BH (e.g., sodium or potassium hydride, or an organometallic base such as sodium diisopropylamide, sodium bis (trimethylsilyl)amide, lithium diisopropylamide, lithium bis (trimethylsilyl)amide, a sodium $C_1$–$C_4$ alkoxide or n-butyllithium), in an appropriate inert solvent such as tetrahydrofuran, acetonitrile, dimethylsulfoxide, acetone, a $C_2$–$C_5$ alcohol, chloroform, benzene, xylene, toluene, N,N-dimethylformamide (DMF), methylene chloride, 1-methyl-2-pyrrolidinone (NMP) or a mixture of two or more of the above solvents (e.g., DMSO and THF), at a temperature from about 0° C. to about 180° C., preferably from about 50° C. to about 180° C.

Compounds of the formula I wherein B is —CR$^1$R$^2$R$^{11}$, —C(C=CR$^2$R$^{12}$)R$^1$, —CR$^2$R$^{11}$NHR$^1$, —CR$^2$R$^{11}$OR$^1$, —CR$^2$R$^{11}$SR$^1$ or —C(O)R$^2$ may be prepared from compounds of the formula III wherein W is cyano, formyl or carboxy, as described below.

Reacting compounds of formula III wherein W is cyano with a Grignard reagent containing the group R$^2$ will yield the corresponding compounds of formula I wherein B is —COR$^2$. Further reaction of the compounds of formula I wherein B is COR$^2$ with a Grignard reagent containing R$^1$ will yield the corresponding the compounds of formula I wherein B is —CR$^1$R$^2$OH. Reacting compounds of formula III wherein W is formyl with a Grignard reagent containing the group R$^2$ will yield the corresponding compounds of the formula I wherein B is —CHR$^2$OH. Suitable solvents for the above Grignard reactions include ethereal solvents such as THF, ether, dioxane and glyme.

Compounds of formula I wherein B is —CR$^1$R$^2$R$^{11}$ or —C(C=CR$^2$R$^{11}$)R$^1$ may be prepared by conventional methods. Thus, reaction of a compound of the formula I wherein B is —CR$^{1'}$R$^{2'}$OH, (wherein R$^{1'}$ and R$^{2'}$ are defined as R$^1$ and R$^2$, respectively, except that R$^{1'}$ may not be R$^1$ and R$^{2'}$ may not be R$^2$), with an acid such as concentrated sulfuric acid in acetic acid, or a Burgess inner salt such as (carboxysulfamoyl)triethylammonium hydroxide methyl ester, will yield a compound of the formula I wherein B is —C(=CR$^2$R$^{11}$)R$^1$. Hydrogenation of a compound of formula I wherein B is —C(=CR$^2$R$^{11}$)R$^1$ using palladium on carbon (Pd/C) or a platinum oxide catalyst in a $C_1$–$C_4$ alkanol solvent, ethyl acetate, benzene or THF will yield a compound of the formula I wherein B is —CHR$^1$R$^2$. Reaction of a compound of the formula I wherein B is —CR$^1$R$^2$OH with diethylaminosulfur trifluoride or triphenylphosphine/carbon tetrachloride in an inert organic solvent such as carbon tetrachloride will afford a compound of the formula I wherein B is —CR$^1$R$^2$F or —CR$^1$R$^2$Cl, respectively.

Reduction of a compound of formula I wherein B is —COR$^2$ with sodium borohydride in an appropriate inert solvent such as a $C_1$–$C_4$ alkanol will yield a compound of the formula I wherein B is —CHR$^2$OH. Alkylation of a compound of the formula I wherein B is —CHR$^2$OH with an alkyl halide (such as alkyl iodide) in the presence of a base such as sodium hydride (NaH) at about room temperature, in an inert organic solvent such as DMF, ether, DMSO, dioxane, or THF, will yield the corresponding compound of the formula I wherein B is —CHR$^2$OR$^1$.

Compounds of the formula I wherein B is —CR$^2$R$^{10}$NHR$^1$ may be prepared by conventional methods such as reductive amination of the corresponding compounds of the formula I wherein B is —C(O)R² with an appropriate amine and reducing agent (such as sodium cyanoborohydride, sodium triacetoxyborohydride or lithium aluminum tetrahydride) in an appropriate inert solvent such as a $C_1$–$C_4$ alkanol or acetic acid.

Conversion of compounds in formula I wherein B is —C(O)R² into compounds in formula I wherein B is —C(S)R² can be accomplished using standard methods well known in the art (e.g., using Lawesson's Reagent or diphosphorus pentasulfide ($P_2S_5$)). Reduction of compounds of the formula I wherein B is —C(S)R² with a reducing agent such as sodium borohydride in a ($C_1$–$C_4$) alkanol or lithium aluminum tetrahydride in THF or ether, at a temperature from about room temperature to about the reflux temperature, gives the corresponding compounds of the formula I wherein B is —CHR²SH. Alkylation of compounds of the formula I wherein B is —CHR²SH with an alkyl halide (such as alkyl iodide) in the presence of a base such as sodium hydride in such an inert solvent such as DMF, at a temperature from about room temperature to about the reflux temperature will afford the corresponding compounds of the formula I wherein B is —CHR²SR¹.

Compounds in formula II may be prepared from compounds of the formula IV or V as described below.

Compounds of formula II wherein T is chloro, bromo or iodo can be prepared by reacting compounds of the formula IV with from one equivalent to an excess of $POT_3$ wherein T is chloro, bromo or iodo, in the presence or absence of a di($C_1$–$C_4$ alkyl)aniline, preferably diethylaniline, with or without a solvent (such as dichloroethane, DMF, dimethylsulfoxide (DMSO) or acetamide), at a temperature from about room temperature to about 180° C., preferably from about 100° C. to about 150° C. Alternatively, compounds of formula II wherein T is chloro, bromo or iodo can be prepared by reacting the corresponding compounds of formula II wherein T is —$OSO_2CF_3$ with a sodium or potassium halide in an appropriate inert solvent such as sulfolane, DMSO, DMF, or acetonitrile, at a temperature from about 60° C. to about 180° C. Compounds of formula II wherein T is —$OSO_2CF_3$ can be prepared by reacting compounds of formula IV with $Tf_2O$ in the presence of a base such as triethylamine or pyridine, in an appropriate inert solvent such as THF, methylene chloride, dioxane, ether or toluene, at a temperature from about 0° C. to about 50° C., preferably from about 0° C. to about room temperature.

Alternatively, compounds of formula II wherein T is chloro, bromo or iodo may be prepared by reacting compounds of formula V with a ($C_1$–$C_7$ alkyl)-nitrite and Cu(I)$T_2$ (wherein T is chloro, bromo or iodo) in an appropriate inert solvent such as acetonitrile, acetone, methylene chloride, THF, dioxane, benzene, toluene, dichloroethane, DMF, DMSO or N-methylpyrrolidinone (NMP) at a temperature from about room temperature to about 150° C., preferably from about 40° C. to about 100° C.

Compounds of formula III wherein W is cyano can be prepared by reacting the corresponding compounds of formula II wherein T is chloro, bromo or iodo with potassium cyanide, copper cyanide, sodium cyanide or a di($C_1$–$C_4$alkyl)aluminum cyanide in an appropriate inert solvent such as dimethylsulfoxide, DMF, toluene or xylene, at temperature from about room temperature to about 180° C., preferably from about 60° C. to about 150° C., with or without Pd(II)OAc or Pd(0)(PPh₃)₄.

Compounds of formula III wherein W is —CHO or —COOH may be prepared by reacting compounds in formula II wherein T is bromo or iodo with an organolithium reagent such as t-BuLi, s-BuLi, or n-BuLi in an appropriate inert solvent such as THF, dioxane, ether, benzene or methylene chloride, at temperature from about –120° C. to about room temperature, preferably from about –110° C. to about –60° C., followed by quenching with an appropriate electrophile such as DMF or $CO_2$ (gas or dry ice), to give compounds of formula III wherein W is —CHO and —COOH, respectively.

It is understood that the general organic chemistry knowledge can be applied to all the cases in which one of the reaction sequences referred to herein can be changed. Changing the reaction sequence is based on the feasibility of a particular reaction at a particular step in a sequence, such as using a protecting group at any stage of a synthesis that is workable, or reducing an ester group to the corresponding $C_1$–$C_4$ alkyl group at any convenient stage of a synthesis. Compounds of formula I wherein R³ is bromo, chloro, —COO($C_1$–$C_4$ alkyl) or —COOH may be converted to the corresponding compounds wherein R³ is ($C_1$–$C_4$ alkyl), —O($C_1$–$C_4$ alkyl), F or —S($C_1$–$C_4$ alkyl) by methods described in the literature. This conversion may not need to be done at the last stage of a particular synthesis, but rather may be more conveniently performed at an earlier stage.

Compounds of formula I or other formulas described herein wherein R³ is —O—($C_1$–$C_4$ alkyl) or —S($C_1$–$C_4$ alkyl) may be prepared by reacting the corresponding compounds wherein R³ is chloro, bromo or iodo with a nucleophile such as a $C_1$–$C_4$ alkanol or a $C_1$–$C_4$ alkanethiol with an organic or inorganic base. Suitable bases for this reaction include sodium and sodium hydride. Compounds of formula I or any of the other formulas described herein wherein R³ is fluoro may be prepared by reacting the corresponding compounds wherein R³ is chloro with tetrabutylammonium fluoride in a suitable inert solvent such as DMSO, methylene chloride or tetrahydrofuran. Tetrahydrofuran is preferred. The reaction temperature can range from about room temperature to about 180° C. Reduction of compound wherein R³ is an ester using $LiAlH_4$/$AlCl_3$ in an appropriate inert solvent such as THF, ether, or dioxane, at temperature from about room temperature to about 100° C., affords the corresponding compound wherein R³ is methyl. Conversion of compounds wherein B is —COOH to the corresponding compounds wherein B is —CO($C_1$–$C_3$ alkyl) may be performed using methods well known in art. Reduction of compounds wherein B is —CO($C_1$–$C_3$ alkyl) using standard literature methods will afford compounds wherein R³ is one of a variety of ($C_1$–$C_4$ alkyl) derivatives.

Compounds of formula IV-a, wherein the right hand side of the six membered ring represents a benzo, pyrido, pyrimido, or pyridazino ring, (R)$_n$ represents from zero to three substituents as defined in formula IV, and R³, R⁵ and R⁷ are as defined above with reference to formula IV, may be prepared, as shown in Scheme 1, starting from compounds of formula VI-a, wherein the 6-membered ring represents a benzo, pyrido, pyrimido, or pyridazino ring, (R)$_n$ represents from zero to three substituents that are the substituents previously defined for the compounds of the formula IV, and X¹ is Br or I. Compounds of formula VII-a may be prepared using Suzuki coupling, Stille coupling or Ullman biaryl synthesis, as described in the literature (See *Tetrahedron Lett.*, 37, 1043–1044, 1996; *Tetrahedron*, 36, 3111–4, 1995; *J. Chem. Soc. Chem. Commun.*, 2551–2553, 1995; *J. Org. Chem.*, 49, 5237–5243, 1984; *Synlett*, 765–766, 1995; *Synlett*, 207, 1992;). Examples of suitable reaction conditions are: (a) reacting a compounds of the formula VI-a wherein X¹ is Br or I with R⁵—B(OH)₂ and a base such as aqueous sodium carbonate, aqueous sodium hydroxide, Ba(OH)₂, $Cs_2CO_3$, $K_3PO_4$, 10% TlOH, sodium or potassium ($C_1$–$C_4$ alkoxide), in the presence of catalytic amount (0.5 mol % to 50% mol %) of a Pd(0) or Pd(II) compound, together with racemic or a chiral phosphino ligand, preferably Pd(PPh$_3$)$_4$, in an appropriate inert solvent such as dimethoxyethane (DME), N,N-dimethylformamide (DMF), benzene, dimethylacetamide (DMA), a $C_1$–$C_6$ alkanol such as ethanol, dioxane, N-methylpyrrolidinone (NMP) or dioxane, at temperature from about 25° C. to about 150° C., preferably from about room temperature to about 120° C.

Alternatively, compounds of formula VII-a may be prepared using methods described in the literature (See *Tetrahedron*, 49, 49–64, 1993; *Chem. Ber.* 93, 2479–2484, 1960; *Can. J. Chem.*, 38, 1445, 1960; *Can. J. Chem.*, 38, 2152–2158, 1960; *Pol. J. Chem.*, 66, 801–805, 1992; *Chem. Pharm. Bull.*, 31, 3460–3464, 1983).

Compounds of formula VIII-a may be prepared using known methods for reducing a nitro group to an amino group. The preferred method is hydrogenation using 5–10% palladium on carbon (Pd/C), at a pressure from about 14 psi to about 55 psi, at about room temperature, in an inert solvent such as ethyl acetate, benzene, THF, or a $C_1$–$C_4$ alkanol.

Compounds of formula IV-a may be prepared by heating compounds of formula VIII-a of compound of the formula $R^3$—C(O)—CH($R^7$)—COO($C_1$–$C_2$ alkyl), in the presence of an acid or Lewis acid, with or without a solvent. Examples of such reaction conditions are: a) heating in polyphosphoric acid; b) heating in toluene, benzene or xylene in the presence of acid catalyst (such as p-TsOH, sulfuric acid, HCl(g)) using Dean-Stark trap apparatus; and c) heating in an appropriate solvent such as dichloroethane, Ph$_2$O or Dowtherm A in the presence of a Lewis acid such as SnCl$_4$, ZnCl$_2$/HCl or AlCl$_3$.

Compounds of formula IV-b and V-a, wherein the right hand side of the six membered ring represents a benzo, pyrido, pyrimido, or pyridazino ring, (R)$_n$ is from zero to three substituents as defined in formula IV, and $R^3$, $R^5$ and $R^7$ are as defined above with reference to formula IV, may be prepared, as shown in Scheme 2, starting from compounds of formula VI-b, wherein the 6-membered ring represents a benzo, pyrido, pyrimido, or pyridazino ring, (R)$_n$ is from zero to three substituents which are the substituents previously defined for the compounds in formula IV, $X^1$ is Br or I and $W^1$ is CN, —CONH$_2$ or —COO($C_1$–$C_2$ alkyl). Conversion of compounds of formula VI-b to VIII-b may be performed by the methods analogous to those described above for the conversion of compounds of the formula VI-a into those of the formula VIII-a. Compounds of the formulas IV-b and V-a may be prepared by heating compounds of formula VIII-b wherein $W^1$ is —COO($C_1$–$C_2$ alkyl) and CN, respectively, with an appropriate $R^3$C(O)CH$_2$COO($C_1$–$C_4$ alkyl) in the presence of a Lewis acid such as SnCl$_4$, AlCl$_3$, TiCl$_3$ or ZnCl$_2$, in dichloroethane, at reflux, as illustrated in Scheme 2. Base hydrolysis of IV-b and V-a with sodium hydroxide in H$_2$O/($C_1$–$C_4$ alcohol) at reflux or with lithium hydroxide in water/THF or water/dioxane at temperature between room temperature to reflux, followed by decarboxylation by heating in an oil bath at a temperature from about 140° C. to about 180° C., to give compounds of formula IV-c and V-b, respectively, Compounds of formula IV-d may be prepared, as shown in Scheme 3, by reacting compounds of formula VIII-b, wherein $W^1$ is —COO($C_1$–$C_2$ alkyl) or —CONH$_2$, with ($R^3$CO)$_2$O or $R^3$COOH or $R^3$C(O$C_1$–$C_2$ alkyl)$_3$ in acetic acid or in an appropriate inert organic solvent such as toluene, dioxane, acetonitrile, methylene chloride or chloroform, at a temperature from between 25° C. to about 150° C., preferably at reflux, followed by heating in 85% phosphoric acid or an aqueous acid about such as acetic acid, hydrochloric acid or sulfuric acid, preferably 50–85% phosphoric acid. Alternatively, heating compounds of formula VIII-b wherein $W^1$ is —COO($C_1$–$C_2$ alkyl) or —CONH$_2$ with a compound of the formula $R^3$CONH$_2$ at a temperature from about 180° C. to about 230° C. will afford a compound of formula IV-d. Compounds of formula V-c may be prepared, as shown in Scheme 3, by heating compounds of the formula VIII-b wherein $W^1$ is CN with an excess of a compound having the formula $R^3$CONH$_2$, at about the reflux temperature.

Compounds of formula I-A, wherein X is O, S, or NR$^8$ may be prepared as illustrated in Scheme 4, starting with compounds of formula IX. Compounds of formula X, wherein $R^4$ is H and X is O may be prepared by reducing the corresponding compounds of formula IX using, for example, LiAlH$_4$ or diisobutylaluminum hydride in THF, ethyl ether or dioxane, at temperature from about room temperature to about the reflux temperature. Compounds of the formula X wherein $R^4$ is hydrogen and X is sulfur may be prepared by standard methods known in literature for the conversion of —CH$_2$OH groups to the corresponding —CH$_2$SH groups. Oxidation of compounds of formula X wherein $R^4$ is H and X is O with PCC (pyridinium chlorochromate) using methods described in the literature will provide the corresponding compounds containing a formyl group. Grignard addition (using a Grignard reagent of the formula $R^4$MgBr) to such formyl group will afford a compound of formula X wherein $R^4$ is as defined previously for formula I. Reductive amination of such formyl group using standard literature methods will provide compounds of the formula X wherein $R^4$ is H and X is N. Alternatively, conversion of the carboxylic acid of compounds of the formula IX into the corresponding —CONR$^8$ groups, followed by reduction using BH$_3$.DMS or LiAlH$_4$ will afford compounds of formula X wherein $R^4$ is H and X is NR$^8$.

Compounds of formulas I-A and I-C may be prepared from compounds of the formulas X and IX, respectively, as illustrated in Scheme 4, by reacting compounds of formula X wherein X is S, NR$^8$, or O with a compound of the formula $R^6$CHO or $R^6$CH(O$C_1$–$C_2$ alkyl)$_2$ and an acid catalyst (such as p-TsOH, HCl, HBr, H$_2$SO$_4$ or HCl) in an inert solvent, such as toluene, xylene or benzene, preferably toluene, with from none to ten equivalents of water, at temperature from about 70° C. to about 160° C., under a Dean-Stark trap apparatus or in the presence of anhydrous sodium sulfate. Compounds of formula I-B and I-D may be prepared by reacting of compounds of formula X and IX, respectively, with triphosgene or thiophosgene and a base such as triethylamine or pyridine in an inert organic solvent such as methylene chloride, THF, dioxane, ether, benzene, chloroform, preferably methylene chloride or dry THF, at temperature from about 0° C. to about 25° C.

Compounds of formula I-G, I-E, I-Q and I-F may be prepared as shown in Scheme 5, starting with compounds of formula X wherein X is OH. Compounds of formula XI may be prepared by reacting compounds of formula X with an excess of thionyl chloride in anhydrous methylene chloride at about room temperature. The solvent and excess of thionyl chloride is then removed and the residue is reacted with compound having the formula of Na—, K— or Li—CR$^4$(COO$C_1$–$C_4$ alkyl)$_2$ or Na—, K— or Li—CR$^4$(CN), in an appropriate solvent such as DMSO, THF, NMP, sulfolane, or a $C_1$–$C_4$ alkanol, at a temperature from about room temperature to about 100° C., preferably at about room temperature. Compounds of formula I-Q may be prepared using standard amide cyclization methods known in literature. Such methods include acid cyclization (such as heating in 40–85% phosphoric acid at a temperature from about 100° C. to about 150° C.; heating in aqueous acetic acid/HCl, or base hydrolysis, decarboxylation, followed by amide cyclization). Compounds of formula I-E may be prepared by bromination of compounds of formula I-Q, followed by base (such DBU or DBN) elimination. Compounds of formula I-F and I-G may be obtained by reducing compounds of the formula of I-Q and I-E, respectively, by standard reduction methods such as heating with $BH_3.DMS$ or $BH_3$ in THF, or with $LiAlH_4$ in THF.

Compounds of formula I-H to I-L wherein $(R)_n$ represents from zero to three substituents such as $R^4$, $R^6$, $R^8$, $R^9$ or $R^{12}$ may be prepared starting with compounds of formula XIII wherein X is $NR^8$, O, or S, as illustrated in Scheme 6. Compounds of the formula XIII may be prepared by reacting the corresponding compounds of formula XII with an acyl halide (such as $X^1CH(R^6)COL$ ($X^1$ is chloro, bromo, iodo, mesylate or tosylate, and L is chloro, bromo or iodo)) in the presence of a base such as a tri-$(C_1–C_4$ alkyl)amine, pyridine or a substituted pyridine, in an appropriate solvent such as methylenechloride, chloroform, THF, DMSO,dioxane, etheror dimethoxyethane (DME), at temperatures from about 0° C. to about 180° C., preferably from about room temperature to about 60° C. Compounds of formula I-H may be prepared by reacting compounds of the formula XIII with a base. Suitable bases for use in this reaction include sodium, sodium hydride, potassium hydride, lithium diisopropylamide, butyl lithium, lithium bis(trimethylsilyl) amide, sodium diisopropylamide and sodium or potassium carbonate. Alkylation of compounds having the formula I-H with a base, followed by quenching with an alkyl halide in an appropriate solvent such as ether, THF, methylene chloride, dioxane, benzene, toluene or DME, with or without HMPA, at a temperature from about −78° C. to about room temperature, will afford compounds of the formula I-J. Suitable bases for this reaction include lithium diisopropylamide, lithium bis(trimethylsilyl)amide sodium diisopropylamide and butyl lithium. Reaction of compounds having the formula I-H or I-J with a reducing agent such as $BH_3.DMS$, $BH_3$, diisbutylaluminum hydride or lithium aluminum hydride will afford compounds of the formula I-K or I-I, respectively. Reaction of compounds of formula I-H or I-J with $POCl_3$ or $PCl_5$, followed by reaction with an organometallic agent containing an $R^6$ group (such as $R^6{}_3Al$ or $R^6{}_2Zn$) will yield compounds of the formula I-I or I-K with an additional $R^6$ substituent at the atom next to the N—$R^5$ moiety.

Compounds of formula I-M to I-P may be prepared, as illustrated in Scheme 7, by methods analogous to those described in Scheme 6. Double bond formation as shown in formulas I-N, I-O, and I-P may be achieved by bromination followed by elimination, using standard methods known in literature. Alternatively, compounds of formula I-N, I-O, and I-P can be prepared by reacting compounds of formula I-M with a base, and the quenching with PhSeSePh, $PhSSO_2Ph$, PhSSOPh, PhSSPh or an equivalent agent, followed by oxidation with $NaIO_4$ and elimination with a base. Monocyclic pyridine or pyrimidine starting agents, such compounds of the formulas IX, X and XIV may be prepared by methods analogous to those described in PCT Patent Application PCT/IB95/00373, which designates the United States and was filed on May 18, 1995 and published on Dec. 21, 1995.

The acid addition salts of compounds of the formula can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The compounds of formula I and their pharmaceutically acceptable salts (hereinafter referred to, collectively, as "the active compounds of this invention") may be administered alone or in combination with pharmaceutically acceptable carriers, in either single or multiple doses. Suitable pharmaceutical carriers include inert solid diluents or fillers, sterile aqueous solutions, oils (e.g., peanut oil, sesame oil) and various organic solvents. The pharmaceutical compositions formed by combining the novel compounds of formula I and pharmaceutically acceptable carriers can then be readily administered in a variety of dosage forms such as tablets, powders, lozenges, emulsions, oil soft gels, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the active compounds of this invention will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastrointestinal diseases, anorexia nervosa, hemorrhagic stress and drug and alcohol withdrawal symptoms will generally range from about 0.1 to about 50 mg/kg body weight of the patient to be treated.

Methods that may be used to determine the CRF antagonist activity of the active compounds of this invention and their pharmaceutically acceptable salts are described in

*Endocrinology*, 116, 1653–1659 (1985) and *Peptides*, 10, 179–188 (1985). The binding activities for compounds of the formula I, expressed as $IC_{50}$ values, generally range from about 0.5 nanomolar to about 10 micromolar.

Methods that can be used to determine the CRF binding protein inhibiting activity of compounds of the formula I are described in *Brain Research*, (1997), 745(1,2), 248–256.

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform ($CDCl_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

The following abbreviations are used in the Examples: Ph=phenyl; iPr=isopropyl; HRMS=high resolution mass spectrum.

EXAMPLE 1

4-(Butyl-ethyl-amino)-2,6-dimethyl-8-(2,4,6-trimethyl-phenyl)-5,8-dihydro-6H-pyrido[2,3-d]pyrimidin-7-one A mixture of 4-chloro-2,6-dimethyl-8-(2,4,6-trimethyl-phenyl)-5,8-dihydro-6H-pyrido[2,3-d]pyrimidin-7-one (75 mg, 0.227 mmol) and N-butyl-ethyl-amine (65 mg, 0.682 mmol) in DMSO (1 ml) was heated in an oil bath of 135° C. for 15 hours. The reaction mixture was quenched with water and extracted with ethyl acetate. The organic layer was dried and concentrated to give 114 mg of the crude material. Silica gel column purification using 5% ethyl acetate in hexane as eluent provided 50 mg of the title compound as a colorless oil. $^1$H NMR ($CDCl_3$) δ 6.95 (s,1H), 6.94(s,1H), 3.2–3.55 (m,4H), 2.88–3.05(dd,1H), 2.70–2.85(m,1H), 2.55–2.70(m, 1H), 2.35(s,3H), 2.25(s,3H), 2.05(s,3H), 1.97(s,3H), 1.5–1.65(m,2H), 1.3–1.5(m,2H), 1.35(d,3H), 1.2(t,3H), 0.98 (t,3H) ppm.

EXAMPLE 2

8-(1-Ethyl-propoxy)-6-methyl-4-(2,4,6-trimethyl-phenyl)-3,4-dihydro-1H-pyrido[2,3-b]pyrazin-2-one To a cooled solution of 2-chloro-N-[4-(1-ethyl-propoxy)-6-methyl-2-(2,4,6-trimethyl-phenylamino)-pyridin-3-yl]-acetamide (40 mg, 0.099 mmol) in dry THF was added 1.0 M lithium bistrimethylsilyl amide ($LiN(SiMe_3)_2$) in THF (0.3 ml, 0.3 mmol) at −78° C. and stirred at that temperature for 1 hour, then warmed to room temperature for 30 min. The mixture was quenched with water and extracted with ethyl acetate. The organic layer was dried and concentrated to give 38 mg of the title compound as a tan crystals. The crystals were purified through silica gel column chromatography using 5% ethyl acetate in hexane as eluent to give 29 mg (81%) of the title compound as a white crystal, mp 179–181° C. $^1$H NMR ($CDCl_3$) δ 7.75(s,1H), 6.95(s,2H), 6.09(s,1H), 4.22(s,2H), 4.22(m,1H), 2.32(s,3H), 2.17(s,3H), 2.16(s,6H), 1.71(m,4H), 0.97(m,6H)ppm.

EXAMPLE 3

8-(1-Ethyl-propoxy)-6-methyl-4-(2,4,6-trimethyl-phenyl)-1,2,3,4-tetrahydro-pyrido[2,3-b]pyrazine A mixture of 8-(1-ethyl-propoxy)-6-methyl-4-(2,4,6-trimethyl-phenyl)-3,4-dihydro-1H-pyrido[2,3-b]pyrazin-2-one (13 mg, 0.0354 mmol) and 2M borane dimethylsulfide complex ($BH_3$.DMS) (0.044 ml, 0.0884 mmol) in 2 ml of dry THF was heated at reflux for 2 hours. The mixture was quenched with 0.2 ml of methanol and 0.2 ml of concentrated hydrochloric acid (HCl) and the resulting mixture was stirred at room temperature for 2 hours, and then concentrated to dryness. The residue was quenched with water, neutralized with saturated sodium bicarbonate and extracted with ethyl acetate. The organic layer was washed with brine, dried and concentrated to give 14.7 mg of the title compound as a brown crystals. The crystals were purified through silica gel column chromatography using 10% ethyl acetate in hexane as eluent to give 9 mg of the title compound as a colorless oil. $^1$H NMR ($CDCl_3$) δ 6.93(s,2H), 6.02(s,1H), 4.18(m,1H), 3.62(m,2H), 3.44(m,2H), 2.31(s,3H), 2.12(s, 9H), 1.71(m,4H), 0.98(t,6H)ppm.

EXAMPLE 4

8-(1-Ethyl-propoxy)-1,6-dimethyl-4-(2,4,6-trimethyl-phenyl)-3,4-dihydro-1H-pyrido[2,3-b]pyrazin-2-one To a −78° C. solution of 8-(1-ethyl-propoxy)-6-methyl-4-(2,4,6-trimethyl-phenyl)-3,4-dihydro-1H-pyrido[2,3-b]pyrazin-2-one (50 mg, 0.136 mmol) in 3 ml of dry THF was added 1.0M of $LiN[Si(CH_3)_3]_2$ in THF (0.14 ml, 0.14 mmol) at −78° C. After stirring at that temperature for 20 min, the reaction mixture was warmed to room temperature and stirred at room temperature overnight. The mixture was quenched with water and saturated ammonium chloride and extracted with ethyl acetate. The organic extract was washed with brine, dried and concentrated to give 51 mg of a golden oil. The oil was purified through silica gel column chromatography using 10% ethyl acetate in hexane as eluent to give 41 mg (79%) of the title compound as a golden oil. $^1$H NMR ($CDCl_3$) δ 6.9(s,2H), 6.17(s,1H), 4.30(m,1H), 4.01(s,2H), 3.47(s,3H), 2.30(s,3H), 2.20(s,3H), 2.01(s,6H), 1.70(m,4H), 0.97(t,6H)ppm.

EXAMPLE 5

4-(1-Ethyl-propoxy)-2-methyl-8-(2,4,6-trimethyl-phenyl)-quinoline

To a solution of 3-pentanol (5.8 ml, 52.7 mmol) in dry THF (5 ml) was added sodium hydride (NaH) portionwise over a period of 10 min. A solution of 4-chloro-2-methyl-8-(2,4,6-trimethyl-phenyl)-quinoline (4.0006 g, 13.52 mmol) in dry THF (10 ml) was added. After stirring at room temperature as for 10 min, 15 ml of dry DMSO was added. The resulting mixture was heated in a 12° C. oil bath for 1.5 hours. The mixture was quenched with water and extracted with EtOAc. The organic layer was separated, dried, filtered, and concentrated to give the title compound as 5.002 g of a yellow solid.

$^1$H NMR ($CDCl_3$) δ 8.19(d,1H), 7.42(m,2H), 6.96(s,2H), 6.53(s,1H), 4.41(m,1H), 2.51(s,3H), 2.36(s,3H), 1.89(s,6H), 1.84(m,4H), 1.02(t,6H)ppm.

The yellow solid was prepared as the corresponding HCl salt and concentrated to dryness. The residue was triturated with hexane to give off-white solid. The solid was recrystallized fron EtOAc to give 4.020 g (78%) of white crystals, mp 153–156° C.

$^1$H NMR ($CDCl_3$) δ 14.05(brs,1H), 8.33(dd,1H), 7.74(m, 1H), 7.66(m,1H), 7.08(s,2H), 6.97(s,1H), 4.76(m,1H), 3.13 (s,3H), 2.06(s,3H), 1.8–2.0(m,4H), 1.91(s,6H), 1.06(t,6H) ppm.

EXAMPLE 6

5-(1-Ethyl-propoxy)-7-methyl-1-(2,4,6-trimethyl-phenyl)-1,4-dihydro-2H-3-oxa-1,8-diaza-naphthalene A mixture of [4-(1-ethyl-propoxy)-6-methyl-2-(2,4,6-trimethyl-phenylamino)-pyridin-3-yl]-methanol (79 mg, 0.231 mmol), 37% aqueous formaldehyde (0.1 ml) and p-TsOH (22 mg, 0.116 mmol) in 10 ml of toluene was heated at reflux using a Dean-Stark apparatus for 3 hours. The mixture was quenched with water and extracted with ethyl acetate. The organic layer was separated, dried and concentrated to give 100 mg of the crude material. The crude material was purified through silica gel column chromatography using 2% methanol in chloroform as eluent to give 40 mg (50%) of the title compound as a clear oil. $^1$H NMR (CDCl$_3$) δ 6.90(s,2H), 6.04(s,1H), 4.87(2 sets of s, 4H), 4.16(m,1H), 2.28(s,3H), 2.19(s,3H), 2.14(s,6H), 1.67(m, 4H), 0.94(t,6H) ppm.

EXAMPLE 7

5-(1-Ethyl-propoxy)-7-methyl-1-(2,4,6-trimethyl-phenyl)-1,2-dihydro-3-oxa-1,8-diaza-naphthalen-4-one The title compound was prepared by the method analogous to that described in Example 6 starting from 4-(1-ethyl-propoxy)-6-methyl-2-(2,4,6-trimethyl-phenylamino)-nicotinic acid to give the title compound as an oil. $^1$H NMR (CDCl$_3$) δ 6.92(s,2H), 6.18(s,1H), 5.21(s,2H), 4.30(m,1H), 2.30(s,3H), 2.25(s,3H), 2.12(s,6H), 1.80(m,4H), 1.02(t,6H) ppm.

EXAMPLE 8

8-(1-Ethyl-propoxy)-1,6-dimethyl-4-(2,4,6-trimethyl-phenyl)-1,2,3,4-tetrahydro-pyrido[2,3-b]pyrazine A mixture of 8-(1-ethyl-propoxy)-1,6-methyl-4-(2,4,6-trimethyl-phenyl)-3,4-dihydro-1H-pyrido[2,3-b]pyrazin-2-one (50 mg, 0.131 mmol) and 2M BH$_3$.DMS (0.16 ml, 0.32 mmol) in 3 ml of dry THF was heated at reflux for 3 hours. The mixture was quenched with 0.5 ml of 1N HCl and the resulting mixture was stirred at room temperature for 20 min, concentrated to dryness. The residue was quenched with water, neutralized with saturated sodium bicarbonate and extracted with ethyl acetate. The organic layer was washed with brine, dried and concentrated to give 38 mg of the title compound as a brown crystals. The crystals was purified through silica gel column chromatography using 10% ethyl acetate in hexane as eluent to give 22 mg of the title compound as a colorless oil. $^1$H NMR (CDCl$_3$) δ 6.91(s,2H), 6.01(s,1H), 4.19(m,1H), 3.44(m,2H), 3.16(m, 2H), 2.77 (s,3H), 2.29(s,3H), 2.12(s,3H), 2.07(s,6H), 1.75 (m,4H), 0.99(t,6H)ppm.

EXAMPLE 9

(1-Ethyl-propl)-[2-methyl-8-(2,4,6-trimethyl-phenyl)-quinolin-4-yl]-amine

A mixture of 4-bromo-2-methyl-8-(2,4,6-trimethyl-phenyl)-quinoline(130 mg, 0.365 mmol), 1-ethylpropylamine (0.13 ml, 1.095 mmol), Pd(OAc)$_2$ (1.7 mg, 0.073 mmol), BINAP(4.55 mg, 0.0073 mmol) and sodium t-butoxide (49 mg, 0.51 mmol) in 2 ml of toluene was heated in 130–150° C. oil bath for 5 hours. The mixture was quenched with water and extracted with I-propyl ether. The organic extract was dried and concentrated to give 160 mg of crude material. The crude material was purified through silica gel column chromatography using 5% to 15% methanol in chloroform as eluent to give 78 mg (62%) of the title compound as a light yellow oil. $^1$H NMR(CDCl$_3$) δ 7.80(m,1H), 7.38(m,1H), 7.33(m,1H), 6.96(s,2H), 6.28(s, 1H), 3.45(m,1H), 2.42(s,3H), 2.36(s,3H), 1.90(s,6H), 1.6–1.8(m,4H), 1.20(t,6H) ppm. The corresponding HCl salt was prepared as a light yellow solid. $^1$H NMR(CDCl$_3$) δ 9.87(brs,1H), 9.80(s,1H), 9.62(d,1H), 7.62(t,1H), 7.44(d, 1H), 6.33(s,1H), 3.62(m,1H), 2.55(s,3H), 2.37(s,3H), 2.34 (s,3H), 2.15(m,4H), 1.87(s,6H), 0.97(t,6H)ppm.

EXAMPLE 10

2-Methyl-4-(tetrahydro-furan-3-yloxy)-8-(2,4,6-trimethyl-phenyl)-quinoline

The title compound was prepared as a light yellow solid starting from 3-hydroxytetrahydrofuran and 4-chloro-2-methyl-8-(2,4,6-trimethyl-phenyl)-quinoline using procedure analogous to that described in Example 5. $^1$H NMR (CDCl$_3$) δ 8.17(d,1H), 7.39–7.46(m,2H), 6.96(s,2H), 6.49 (s,1H), 5.13(m,1H), 4.14(d,2H), 3.8–4.1(m,4H), 2.51(s,3H), 2.36(s,3H), 2.15–2.20(m,2H), 1.89(s,6H)ppm.

EXAMPLE 11

5-(1-Ethyl-propoxy)-7-methyl-1-(2,4,6-trimethyl-phenyl)-3,4-dihydro-1H-[1,8]naphthyridin-2-one A mixture of 2-[4-(1-ethyl-propylamino)-6-methyl-2-(2, 4,6-trimethyl-phenylamino)-pyridin-3-ylmethyl]-malonic acid dimethyl ester (100 mg, 0.219 mmol), 85% phosphoric acid (3 ml) and water (3 ml) was heated at reflux for 2 hours. The reaction mixture was cooled to room temperature, diluted with water and extracted with ethyl acetate. The organic layer was washed with brine, dried over anhydrous MgSO$_4$, filtered and concentrated to dryness to give 91 mg of a clear oil. The oil was purified through silca gel column chromatography using 10% methanol (MeOH) in methylene chloride (CHCl$_2$) as eluent to give a tan crystals, mp 138–140° C. $^1$H NMR (CDCl$_3$) δ 6.93(s,2H), 6.31(s,1H), 4.21(m,1H), 2.93(m,2H), 2.76(m,2H), 2.31(s,3H), 2.19(s, 3H), 1.99(s,6H), 1.71(m,4H), 0.96(t,6H) ppm.

EXAMPLE 12

5-(1-Ethyl-propylamino)-7-methyl-1-(2,4,6-trimethyl-phenyl)-3,4-dihydro-1H-[1,8]naphthyridin-2-one The title compound was prepared as a tan solid, mp 124–126° C., using a method analogous to that described in the Example 11, starting from 2-[4-(1-ethyl-propylamino)-6-methyl-2-(2,4,6-trimethyl-phenylamino)-pyridin-3-ylmethyl]-malonic acid dimethyl esterand aqueous phosphoric acid. $^1$H NMR (CDCl$_3$) δ 6.91(s,2H), 6.09(s,1H), 3.68 (d,1H), 3.33(m,1H), 2.82(m,2H), 2.67(m,2H), 2.30(s,3H), 2.12(s,3H), 1.99(s,6H), 1.5–1.7(m,4H), 0.94(t,6H) ppm.

EXAMPLE 13

5-(1-Ethyl-propoxy)-7-methyl-1-(2,4,6-trimethyl-phenyl)-3,4-dihydro-1H-pyrido[2,3-d]pyrimmidin-2-one To a mixture of 3-aminomethyl-4-N-(1-ethyl-propyl)-6-methyl-2-N-(2,4,6-trimethyl-phenyl)-pyridine-2,4-diamine (100 mg, 0.293 mmol) in dry THF was added triphosgene (34 mg, 0.114 mmol) at 0° C. The reaction mixture was allowed to gradually warm to room temperature and was stirred for 1 hour. The mixture was quenched with water and extracted with ethyl acetate. The organic layer was dried and concentrated to dryness to give 100 mg (92.5%) of a tan solid. The solid was purified through silica gel column chromatography using 20% to 40% EtOAc in hexane as the eluent to give 75 mg (69.4%) of the title compound as a white crystalline solid, mp 258–260° C. $^1$H NMR (CDCl$_3$) δ 6.92(s,2H), 6.24(s,1H), 5.19(s,1H), 4.48(s,2H), 4.20(m, 1H), 2.30(s,3H), 2.19(s,3H), 2.07(s,6H), 1.67(m,4H), 0.94 (t,6H) ppm.

EXAMPLE 14

4-(1-Ethyl-propoxy)-2,6-dimethyl-8-(2,4,6-trimethyl-phenyl)-8H-pteridin-7-one

To a solution of 6-(1-ethyl-propoxy)-2-methyl-4-N-(2,4,6-trimethyl-phenyl)-pyrimidine-4,5-diamine (100 mg, 0.305 mmol) in 2 ml of ethanol was added pyruvic acid (30 mg, 0.335 mmol) and the resulting mixture was heated at reflux for 1 hour. An additional 60 mg of pyruvic acid was added and the resulting mixture was heated at reflux overnight. The mixture was quenched with water and extracted with chloroform. The organic layer was washed with water and brine, dried over sodium sulfate, filtered and concentrated to give an oil residue. The residue was purified through silica gel column chromatography using hexane to 15% ethyl acetate in hexane as eluent to give the title compound as a yellow solid. $^1$H NMR (CDCl$_3$) δ 6.99 (s,2H), 5.39(m,1H), 2.61(s, 3H), 2.40(s,3H), 2.35(s,3H), 1.88(s,6H), 1.7–1.9(m,4H), 0.99(t,6H)ppm.

EXAMPLE 15

5-(1-Ethyl-propoxy)-7-methyl-1-(2,4,6-trimethyl-phenyl)-1,2,3,4-tetrahydro-[1,8]naphthyridine The title compound was prepared in a 86% yield as a clear oil by the method analogous to that described in Example 8 starting from 5-(1-ethyl-propoxy)-7-methyl-1-(2,4,6-trimethyl-phenyl)-3,4-dihydro-1H-[1,8]naphthyridin-2-one and BH3.DMS in THF.
$^1$H NMR (CDCl$_3$) δ 6.90(s,2H), 5.95(s,1H), 4.13(m,1H), 3.40(m,2H), 2.71(m,2H), 2.28(s,3H), 2.14(s,3H), 2.08(s, 6H), 1.99(m,2H), 1.67(m,4H), 0.94(t,6H) ppm.

EXAMPLE 16

8-(1-Ethyl-propoxy)-2,6-dimethyl-4-(2,4,6-trimethyl-phenyl)-4H-pyrido[2,3-b]pyrazin-3-one A mixture of 4-(1-ethyl-propoxy)-6-methyl-N-2-(2,4,6-trimethyl-phenyl)-pyridine-2,3-diamine (250 mg, 0.763 mmol) and pyruvic acid (67 mg, 0.763 mmol) in 8 ml of EtOH was heated at reflux overnight. The reaction mixture was cooled and a pale yellow crystalline precipitate formed and filtered to give 83 mg of the title compound, mp 215–217° C. The filtrate was concentrated to dryness to give an additional 200 mg of the desired product as a yellow solid. $^1$H NMR (CDCl$_3$) δ 6.98(s,2H), 6.53(s,1H), 4.37(m, 1H), 2.61(s,3H), 2.34(s,3H), 1.87(s,6H), 1.8–2.0(m,4H), 1.04(t,6H)ppm.

The title compounds of Examples 17 and 18 were isolated starting from 4-(1-ethyl-propoxy)-6-methyl-2-(2,4,6-trimethyl-phenylamino)-nicotinamide and triphosgene, using a method analogous to that described in Example 13.

EXAMPLE 17

4-Chloro-5-(1-ethyl-propoxy)-7-methyl-1-(2,4,6-trimethyl-phenyl)-1H-pyrido[2,3-d]pyrimidin-2-one A white crystal, mp 125–127° C. $^1$H NMR (CDCl$_3$) δ 6.93(s,3H), 6.56(s,1H), 4.31(m,1H), 2.35(s,3H), 2.34(s,6H), 2.30(s,3H), 1.76(m,4H), 0.97(t,6H) ppm.

EXAMPLE 18

5-(1-Ethyl-propoxy)-7-methyl-1-(2,4,6-trimethyl-phenyl)-1H-pyrido[2,3-d]pyrimidine-2,4-dione A white crystal, mp 105–107° C. $^1$H NMR (CDCl$_3$) δ 6.90(s,2H), 6.26(brs,1H), 6.05(s,1H), 4.24(m,1H), 2.29(s, 3H), 2.25(s,3H), 2.17(s,6H), 1.71(m,4H), 0.97(t,6H) ppm.

The title compounds of Examples 19 and 20 were prepared starting from [2-(4-bromo(or chloro)-2,6-dimethyl-phenylamino)-4-(1-ethyl-propoxy)-6-methyl-pyridin-3-yl]-methanol and 37% aqueous formaldehyde using a procedure analogous to that described in Example 6.

EXAMPLE 19

1-(4-Bromo-2,6-dimethyl-phenyl)-5-(1-ethyl-propoxy)-7-methyl-1,4-dihydro-2H-3-oxa-1,8-diaza-naphthalene The parent compound is a clear oil. $^1$H NMR (CDCl$_3$) δ 7.20 (s,2H), 6.05(s,1H), 4.85(s,2H), 4.83(s,2H), 4.14(m, 1H), 2.17(s,3H), 2.12(s,6H), 1.65(m,4H), 0.92(t,6H) ppm. The HCl salt, a white solid, mp 206–209° C. $^1$H NMR (CDCl$_3$) δ 14.5(brs,1H), 7.31(s,2H), 6.23(s,1H), 4.84(s,2H), 4.81(s,2H), 4.34(m,1H), 2.76(s,3H), 2.20(s,6H), 1.72(m, 4H), 0.94(t,6H) ppm.

EXAMPLE 20

1-(4-Chloro-2,6-dimethyl-phenyl)-5-(1-ethyl-propoxy)-7-methyl-1,4-dihydro-2H-3-oxa-1,8-diaza-naphthalene The parent compound is a clear oil. $^1$H NMR (CDCl$_3$) δ 7.07 (s,2H), 6.07(s,1H), 4.87(s,2H), 4.85(s,2H),4.17(m,1H), 2.19(s,3H), 2.15(s,6H), 1.67(m,4H), 0.95(t,6H) ppm. The HCl salt, a white solid, mp 190–192° C. $^1$H NMR (CDCl$_3$) d 14.5(brs,1H), 7.26(s,2H), 6.27(s,1H), 4.87(s,2H), 4.85(s, 2H), 4.37(m,1H), 2.78(s,3H), 2.23(s,6H), 1.74(m,4H), 0.97 (t,6H) ppm.

Preparation A

2-Chloro-N-[4-(1-ethyl-propoxy)-6-methyl-2-(2,4,6-trimethyl-phenylamino)-pyridin-3-yl]-acetamide To a solution of 4-(1-ethyl-propoxy)-6-methyl-N2-(2,4,6-trimethyl-phenyl)-pyridine-2,3-diamine (103 mg, 0.315 mmol) in 4 ml of dry THF was added chloroacetyl chloride (36 mg, 0.315 mmol) and triethylamine (32 mg, 0.315 mmol) at 0° C. The mixture was warmed to room temperature and stirred at room temperature overnight. The mixture was quenched with water and extracted with ethyl acetate. The organic layer was dried and concentrated to give 125 mg of brown residue. The brown residue was purified through silica gel column chromatography using 10% ethyl acetate in hexaneas eluentto give 59 mg of the title compounds as a tan solid, mp 79–82° C. $^1$H NMR (CDCl$_3$) δ 8.15(brs,1H), 6.87(s,2H), 6.78(s,1H), 6.14(s,1H), 4.20(m,1H), 4.19(s,2H), 2.28(s,3H), 2.24(s,3H), 2.16(s,6H).

Preparation B

4-Chloro-2,6-dimethyl-8-(2,4,6-trimethyl-phenyl)-5,8-dihydro-6H-pyrido[2,3-d]pyrimidin-7-one A mixture of 3-[4-chloro-2-methyl-6-(2,4,6-trimethyl-phenylamino)-pyrimidin-5-yl]-2-methyl-propionic acid ethyl ester (173 mg, 0.46 mmol) and p-TsOH (56 mg) in 10 ml of toluene was heated at reflux using Dean-stark trap apparatus for 9 hours. The mixture was quenched with water and extracted with ethyl acetate. The organic extract was washed with brine, dried and concentrated to give 184 mg of the crude material. The crude material was purified through silica gel column chromatography using 10% ethyl acetate in hexane as eluent to give 95 mg of the title compound as white crystals, mp 136–139° C., after recrystallization from ethyl ether. $^1$H NMR (CDCl$_3$) δ 6.95(s,1H), 6.94(s,1H), 3.25(dd,1H), 2.8–3.0(m,2H), 2.41(s,3H), 2.32(s,3H), 1.96(s,3H), 1.93(s,3H), 1.37(d,3H)ppm.

Preparation C

2-Methyl-8-(2,4,6-trimethyl-phenyl)-quinolin-4-ol

A mixture of 2',4',6'-trimethyl-biphenyl-2-ylamine(607 mg, 2.88 mmol) and methyl acetylacetone (607 mg, 5.75 mmol) in polyphosphoric acid (3 ml) was heated in 170° C. oil bath for 2.5 hours. The mixture was quenched with water and extracted twice with chloroform. The organic layer was washed with brine, dried and concentrated to give the title compound as an oil. The oil was pumped in vacuo, then trituated with a mixture of ether and hexane to give 642 mg (81%) of the title compound as a beige solid. The solid was recrystallized from ethyl acetate to give a beige solid, mp>250° C.
$^1$H NMR (CDCl$_3$) δ 8.31(d,1H), 7.9(brs,1H), 7.40(m,1H), 7.34(m,1H), 7.01(s,2H), 6.26(s,1H), 2.33(s,3H), 2.26(s,3H), 1.6(s,3H), 1.93(s,3H), 1.37(d,3H)ppm.

Preparation D

4-Chloro-2-methyl-8-(2,4,6-trimethyl-phenyl)-quinoline

A mixture of 2-methyl-8-(2,4,6-trimethyl-phenyl)-quinolin-4-ol(335 mg, 1.21 mmol) and POCl$_3$(2.5 ml) was heated in 130° C. oil bath for 3 hours. The mixture was cooled and poured into ice-water and extracted with ethyl acetate. The organic layer was washed with brine, dried and concentrated to give 350 mg of crude material as a brown oil. The oil residue was purified through silica gel column chromatography using chloroform as eluent to give 316 mg (87%) of the title compound as a yellow oil. $^1$H NMR (CDCl$_3$) δ 8.20(d,1H), 7.60(m,1H), 7.47(d,1H), 7.35(s,1H), 6.97(s,2H), 2.54(s,3H), 2.36(s,3H), 1.86(s,6H)ppm.

Preparation E

Trifluoro-methanesulfonic acid 2-methyl-8-(2,4,6-trimethyl-phenyl)-quinolin-4-yl ester A mixture of 2-methyl-8-(2,4,6-trimethyl-phenyl)-quinolin-4-ol(416 mg, 1.5 mmol), triflic anhydride (508 ml., 1.8 mmol) and triethylamine (182 mg, 1.8 mmol) in 5 ml of methylene chloride was stirred at room temperature for 1 hour. The mixture was quenched with water and extracted with chloroform. The organic layer was washed with brine, dried and concentrated to give 587 mg of the title compound as a brown glass form. The material was used directly for the next reaction. $^1$H NMR (CDCl$_3$) δ 8.02(d,1H), 7.65(t,1H), 7.55(d,1H), 7.24(s,1H), 6.97(s,2H), 2.62(s,3H), 2.37(s,3H), 1.85(s,6H)ppm.

Preparation F

4-Bromo-2-methyl-8-(2,4,6-trimethyl-phenyl)-quinoline

A mixture of trifluoro-methanesulfonic acid 2-methyl-8-(2,4,6-trimethyl-phenyl)-quinolin-4-yl ester (426 mg, 1 mmol) and potassium bromide (KBr) (809 mg, 1.1 mmol) in a mixture of 1 ml of dry DMSO and 3 ml of dry THF was heated in 120° C. oil bath for 3 hours. The mixture was quenched with water, extracted with ethyl acetate. The organic layer was dried and concentrated to give 358 mg of the title compound as an off-white solid. $^1$H NMR (CDCl$_3$) δ 8.16 (m,1H), 7.59 (m,1H), 7.56(s,1H), 7.48(m,1H), 6.97 (s,1H), 2.53(s,3H), 2.37(s,3H), 1.87(,6H) ppm.

What is claimed is:

1. A compound of the formula

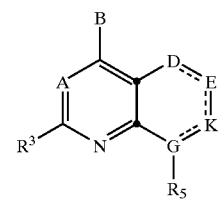

the dashed lines represent optional double bonds;

A is CR$^7$;

B is —NR$^1$R$^2$, —CR$^1$R$^2$R$^{10}$, —C(=CR$^2$R$^{11}$)R$^1$, —NHCR$^1$R$^2$R$^{10}$, —OCR$^1$R$^2$R$^{10}$, —SCR$^1$R$^2$R$^{10}$, —CR$^2$R$^{10}$NHR$^1$, —CR$^2$R$^{10}$OR$^1$, —CR$^2$R$^{10}$SR$^1$ or —COR$^2$;

G is carbon and is double bonded to K;

K is CR$^6$,

D and E are each, independently, C=O, C=S, sulfur, oxygen, CR$^4$R$^6$ when single bonded to both adjacent ring atoms, or CR$^4$ when it is double bonded to an adjacent ring atom;

R$^1$ is C$_1$–C$_6$ alkyl optionally substituted with from one or two substituents independently selected from hydroxy, fluoro, chloro, bromo, iodo, C$_1$–C$_4$ alkoxy, CF$_3$, —C(=O)(C$_1$–C$_4$alkyl), —C(=O)—O—(C$_1$–C$_4$) alkyl, —OC(=O)(C$_1$–C$_4$ alkyl), —OC(=O)N(C$_1$–C$_4$ alkyl)(C$_1$–C$_2$ alkyl), —NHCO(C$_1$–C$_4$ alkyl), —COOH, —COO(C$_1$–C$_4$ alkyl), —CONH(C$_1$–C$_4$ alkyl), —CON(C$_1$–C$_4$ alkyl)(C$_1$–C$_2$ alkyl), —S(C$_1$–C$_4$ alkyl), —CN, —NO$_2$, —SO(C$_1$–C$_4$ alkyl), —SO$_2$(C$_1$–C$_4$ alkyl), —SO$_2$NH(C$_1$–C$_4$ alkyl) and —SO$_2$N(C$_1$–C$_4$ alkyl)(C$_1$–C$_2$ alkyl), wherein each of the C$_1$–C$_4$ alkyl groups in the foregoing R$^1$ groups may optionally contain one or two double or triple bonds;

R$^2$ is C$_1$–C$_{12}$ alkyl which may optionally contain from one to three double or triple bonds, aryl or (C$_1$–C$_4$ alkylene)aryl, wherein said aryl and the aryl moiety of said (C$_1$–C$_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; C$_3$–C$_8$ cycloalkyl or (C$_1$–C$_6$ alkylene)(C$_3$–C$_8$ cycloalkyl), wherein one or two of the carbon atoms of said cycloalkyl and the 5 to 8 membered cycloalkyl moieties of said (C$_1$–C$_6$ alkylene)(C$_3$–C$_8$ cycloalkyl may optionally and independently be replaced by an oxygen or sulfur atom or by NZ wherein Z is hydrogen, C$_1$–C$_4$ alkyl or benzyl, and wherein each of the foregoing R$^2$ groups may optionally be substituted with from one to three substituents independently selected from chloro, fluoro, hydroxy and C$_1$–C$_4$ alkyl, or with one substituent selected from C$_1$–C$_6$ alkoxy, —OC(=O)(C$_1$–C$_6$ alkyl), —OC(=O)N(C$_1$–C$_4$ alkyl)

($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl);

—NR$^1$R$^2$ or CR$^1$R$^2$R$^{10}$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by NZ$^2$ wherein Z$^2$ is hydrogen, benzyl or $C_1$–$C_4$ alkyl;

R$^3$ is hydrogen, $C_1$–$C_4$ alkyl, —O($C_1$–$C_4$ alkyl), chloro, fluoro, bromo, iodo, —S($C_1$–$C_4$ alkyl) or —SO$_2$($C_1$–$C_4$ alkyl);

each R$^4$ that is attached to a carbon atom is selected, independently, from hydrogen and $C_1$–$C_6$ alkyl, fluoro, chloro, iodo, hydroxy, hydroxy ($C_1$–$C_2$ alkyl), trifluoromethyl, cyano, amino, nitro, —O($C_1$–$C_4$ alkyl), —N($C_1$–$C_4$ alkyl)($C_1$–$C_2$ alkyl), —CH$_2$SCH$_3$, —S($C_1$–$C_4$ alkyl), —CO($C_1$–$C_4$ alkyl), —C(=O)H or —C(=O)O($C_1$–$C_4$ alkyl), wherein each of the $C_1$–$C_2$ alkyl moieties in the foregoing R$^4$ groups may optionally contain one double or triple bond;

each R$^6$ that is attached to a carbon atome is selected, independently, from hydrogen and $C_1$–$C_6$ alkyl, fluoro, chloro, bromo, iodo, hydroxy, hydroxy ($C_1$–$C_2$ alkyl), trifluoromethyl, cyano, amino, nitro, —O($C_1$–$C_4$ alkyl), —N($C_1$–$C_4$ alkyl)($C_1$–$C_2$ alkyl), —CH$_2$SCH$_3$, —S($C_1$–$C_4$ alkyl), —CO($C_1$–$C_4$ alkyl), —C(=O)H or —C(=O)O($C_1$–$C_4$ alkyl), wherein each of the $C_1$–$C_2$ alkyl moieties in the foregoing R$^6$ groups may optionally contain one double or triple bond;

R$^5$ is substituted phenyl, naphthyl, pyridyl or pyrimidyl, wherein each of the foregoing R$^5$ groups is substituted with from two to four substituents R$^{13}$, wherein up to three of said substituents may be selected, independently, from chloro, $C_1$–$C_6$ alkyl, —O($C_1$–$C_6$ alkyl) and —($C_1$–$C_6$ alkylene)O($C_1$–$C_6$alkyl), and wherein one of said substituents may be selected, independently, from bromo, iodo, formyl, cyano, trifluoromethyl, nitro, amino, —NH($C_1$–$C_4$ alkyl), —N($C_1$–$C_2$ alkyl)($C_1$–$C_6$ alkyl), —C(=O)O($C_1$–$C_4$ alkyl), —C(=O)($C_1$–$C_4$ alkyl), —COOH, —SO$_2$NH ($C_1$–$C_4$ alkyl), —SO$_2$N($C_1$–$C_2$ alkyl)($C_1$–$C_4$ alkyl), —SO$_2$NH$_2$, —NHSO$_2$($C_1$–$C_4$ alkyl), —($C_0$–$C_1$alkylene)-S—($C_1$–$C_2$alkyl), —($C_0$–$C_1$alkylene)-SO—($C_1$–$C_2$alkyl), —($C_0$–$C_1$alkylene)-SO$_2$—($C_1$–$C_2$alkyl) and —($C_1$–$C_4$alkylene)-OH, and wherein each of the $C_1$–$C_4$ alkyl and $C_1$–$C_6$ alkyl moieties in the foregoing R$^5$ groups may optionally be substituted with one or two substituents independently selected from fluoro, hydroxy, amino, methylamino, dimethylamino and acetyl;

R$^7$ is hydrogen, methyl, halo, hydroxy, methoxy, —C(=O)($C_1$–$C_2$ alkyl), —C(=O)O($C_1$–$C_2$ alkyl), hydroxymethyl, trifluoromethyl or formyl;

R$^{10}$ is hydrogen, hydroxy, methoxy or fluoro; and

R$^{11}$ is hydrogen or $C_1$–$C_4$ alkyl;

with the proviso that in the ring containing D, E, K and G of formula I, there can not be two double bonds adjacent to each other; or a pharmaceutically acceptable salt of such compound.

2. A compound according to claim 1 wherein B is —NR$^1$R$^2$, —NHCHR$^1$R$^2$ or —OCHR$^1$R$^2$ and R$^1$ is $C_1$–$C_6$ alkyl, which may optionally be substituted with one fluoro, or $C_1$–$C_4$ alkoxy group and may optionally contain one double or triple bond; and R$^2$ is $C_1$–$C_4$ alkyl or —($C_1$–$C_2$ alkyl)-CO—($C_1$–$C_2$ alkyl) which may optionally contain one double or triple bond.

3. A compound according to claim 1 wherein B is —CHR$^1$R$^2$, —NR$^1$R$^2$, —NHCHR$^1$R$^2$, —OCHR$^1$R$^2$ or —SCHR$^1$R$^2$, and R$^1$ is $C_1$–$C_6$ alkyl, which may optionally be substituted with one hydroxy, cyclopropylfluoro, CF$_3$ or $C_1$–$C_4$ alkoxy group and may optionally contain one double or triple bond; and R$^2$ is benzyl or $C_1$–$C_6$ alkyl, which may optionally contain one double or triple bond, wherein said $C_1$–$C_6$ alkyl and the phenyl moiety of said benzyl may optionally be substituted with one fluoro, cyclopropyl, hydroxy, CF$_3$, $C_1$–$C_2$ alkyl, $C_1$–$C_2$ alkoxy or chloro group.

4. A compound according to claim 1 wherein A is CH or CH$_3$.

5. A compound according to claim 1 wherein the ring containing D, E, K and G is a benzo ring.

6. A compound according to claim 1 wherein R$^3$ is methyl and each of R$^4$, R$^6$, R$^8$, R$^9$ and R$^{12}$ is hydrogen.

7. A compound according to claim 1 wherein R$^5$ is di- or tri-substituted phenyl in which the two or three substitutents are independently selected from $C_1$–$C_4$ alkyl, —O—($C_1$–$C_4$ alkyl), —($C_1$–$C_4$ alkylene)-O—($C_1$–$C_4$ alkyl), CF$_3$, —OCF$_3$, —CHO, —($C_1$–$C_4$ alkylene)-OH, cyano, chloro, fluoro, bromo and iodo, wherein each of the forgoing ($C_1$–$C_4$) alkyl groups may optionally contain one double or triple bond.

8. A compound according to claim 1 wherein R$^3$ is methyl, ethyl, chloro or methoxy and each R$^4$, R$^6$, R$^8$, R$^9$, and R$^{12}$ is, independently, hydrogen or methyl.

9. A compound according to claim 1 wherein R$^5$ is di- or tri-substituted phenyl, pyridyl, or pyrimidyl in which the two or three substitutents are independently selected from $C_1$–$C_4$ alkyl, —O—($C_1$–$C_4$ alkyl), —($C_1$–$C_4$ alkylene)-O—($C_1$–$C_4$ alkyl), CF$_3$, —OCF$_3$, —CHO, —($C_1$–$C_4$ alkylene)-OH, cyano, chloro, fluoro, bromo and iodo, wherein each of the forgoing ($C_1$–$C_4$) alkyl groups may optionally contain one double or triple bond.

10. A compound according to claim 1 wherein B is —CHR$^1$R$^2$, —NCHR$^1$R$^2$ or —OCHR$^1$R$^2$, and the CHR$^1$R$^2$ group of B is a cyclopentane ring, a tetrahydrofuran ring or a tetrahydrothienyl ring.

11. A compound according to claim 1, wherein said compound is:

(1-Ethyl-propyl)-[2-methyl-8-(2,4,6-trimethyl-phenyl)-quinolin-4-yl]-amine;

4-(1-Ethyl-propoxy)-2-methyl-8-(2,4,6-trimethyl-phenyl)-quinoline;

2-Methyl-4-(tetrahydro-furan-3-yloxy)-8-(2,4,6-trimethyl-phenyl)-quinoline;

or a pharmaceutically acceptable salt of such compound.

12. A compound according to claim 1, wherein D and E are each CR$^4$ when double bonded to each other and CR$^4$R$^6$ when single bonded to each other.

13. A compound of the formula

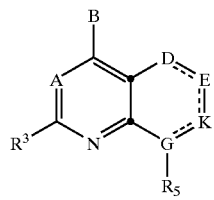

wherein the dashed lines represent optional double bonds;

A is $CR^7$;

B is —$CHR^1R^2$, —$NR^1R^2$, —$NHCHR^1R^2$, —$OCHR^1R^2$ or —$SCHR^1R^2$,

G is carbon and is double bonded to K;

K is $CR^6$,

D and E are each, independently, C=O, C=S, sulfur, oxygen, $CR^4R^6$ when single bonded to both adjacent ring atoms, or $CR^4$ when it is double bonded to an adjacent ring atom;

$R^1$ is $C_1$–$C_6$ alkyl which may optionally be substituted with one hydroxy, cyclopropylfluoro, $CF_3$ or $C_1$–$C_4$ alkoxy group and may optionally contain one double or triple bond;

$R^2$ is benzyl or $C_1$–$C_6$ alkyl, which may optionally contain one double or triple bond, wherein said $C_1$–$C_6$ alkyl and the phenyl moiety of said benzyl may optionally be substituted with one fluoro, cyclopropyl, hydroxy, $CF_3$ or $C_1$–$C_2$ alkyl, $C_1$–$C_2$ alkoxy or chloro group;

—$NR^1R^2$ or —$CHR^1R^2$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by $NZ^2$ wherein $Z^2$ is hydrogen, benzyl or $C_1$–$C_4$ alkyl;

$R^3$ is hydrogen, $C_1$–$C_4$ alkyl, —$O(C_1$–$C_4$ alkyl), chloro, fluoro, bromo, iodo, —$S(C_1$–$C_4$ alkyl) or —$SO_2(C_1$–$C_4$ alkyl);

each $R^4$ and $R^6$ that is attached to a carbon atom is selected, independently, from hydrogen and $C_1$–$C_6$ alkyl, fluoro, chloro, iodo, hydroxy, hydroxy ($C_1$–$C_2$ alkyl), trifluoromethyl, cyano, amino, nitro, —$O(C_1$–$C_4$ alkyl), —$N(C_1$–$C_4$ alkyl)($C_1$–$C_2$ alkyl), —$CH_2SCH_3$, —$S(C_1$–$C_4$ alkyl), —$CO(C_1$–$C_4$ alkyl), —C(=O)H or —C(=O)O($C_1$–$C_4$ alkyl), wherein each of the $C_1$–$C_2$ alkyl moieties in the foregoing $R^4$ and $R^6$ groups may optionally contain one double or triple bond;

$R^5$ is substituted phenyl, naphthyl, pyridyl or pyrimidyl, wherein each of the foregoing $R^5$ groups is substituted with from two to four substituents $R^{13}$, wherein up to three of said substituents may be selected, independently, from chloro, $C_1$–$C_6$ alkyl, —$O(C_1$–$C_6$ alkyl) and —$(C_1$–$C_6$ alkylene)$O(C_1$–$C_6$alkyl), and wherein one of said substituents may be selected, independently, from bromo, iodo, formyl, cyano, trifluoromethyl, nitro, amino, —$NH(C_1$–$C_4$ alkyl), —$N(C_1$–$C_2$ alkyl)($C_1$–$C_6$ alkyl), —C(=O)O($C_1$–$C_4$ alkyl), —C(=O)($C_1$–$C_4$ alkyl), —COOH, —$SO_2NH(C_1$–$C_4$ alkyl), —$SO_2N(C_1$–$C_2$ alkyl)($C_1$–$C_4$ alkyl), —$SO_2NH_2$, —$NHSO_2(C_1$–$C_4$ alkyl), —$(C_0$–$C_1$-alkylene)-S—($C_1$–$C_2$alkyl), —$(C_0$–$C_1$alkylene)-SO—($C_1$–$C_2$alkyl), —$(C_0$–$C_1$alkylene)-$SO_2$—($C_1$–$C_2$alkyl) and —$(C_1$–$C_4$alkylene)-OH, and wherein each of the $C_1$–$C_4$ alkyl and $C_1$–$C_6$ alkyl moieties in the foregoing $R^5$ groups may optionally be substituted with one or two substituents independently selected from fluoro, hydroxy, amino, methylamino, dimethylamino and acetyl; and $R^7$ is hydrogen, methyl, halo, hydroxy, methoxy, —C(=O)($C_1$–$C_2$ alkyl), —C(=O)O($C_1$–$C_2$ alkyl), hydroxymethyl, trifluoromethyl or formyl;

with the proviso that in the ring containing D, E, K and G of formula I, there can not be two double bonds adjacent to each other; or a pharmaceutically acceptable salt of such compound, wherein the ring containing D, E, K, and G is a benzo ring.

14. A compound according to claim 13, wherein $R^3$ is methyl.

15. A compound according to claim 14, wherein $R^5$ is di- or tri-substituted phenyl at the ortho or para positions in which the two or three substituents are independently selected from $C_1$–$C_4$ alkyl, cyclopropyl, —O—($C_1$–$C_4$ alkyl), —($C_1$–$C_4$ alkylene)-O—($C_1$–$C_4$ alkyl), $CF_3$, $OCF_3$, CHO, —($C_1$–$C_4$ alkylene)-OH, chloro, fluoro, bromo and iodo, wherein each of the foregoing $C_1$–$C_4$ alkyl groups may optionally contain one double or triple bond.

16. A compound according to claim 14, wherein $R^5$ is di- or tri-substituted pyridyl at the ortho or para positions in which the two or three substituents are independently selected from $C_1$–$C_4$ alkyl, cyclopropyl, —O—($C_1$–$C_4$ alkyl), —($C_1$–$C_4$ alkylene)-O—($C_1$–$C_4$ alkyl), $CF_3$, $OCF_3$, CHO, —($C_1$–$C_4$ alkylene)-OH, chloro, fluoro, bromo and iodo, wherein each of the foregoing $C_1$–$C_4$ alkyl groups may optionally contain one double or triple bond.

17. A pharmaceutical composition for the treatment, of a disorder slected from inflammatory disorders, pain, asthma, psoriasis and allergies; generalized anxiety disorder; panic; phobias; obsessive-compulsive disorder; post-traumatic stress disorder; sleep disorders induced by stress; pain perception; mood disorders; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus (HIV) infections; neurodegenerative diseases; gastrointestinal diseases; eating disorders: hemorrhagic stress; chemical dependencies and addictions; drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage; excitotoxic neuronal damage; epilepsy; stroke; immune dysfunctions including stress induced immune dysfunctions; muscular spasms; urinary incontinence; senile dementia of the Alzheimer's type; multiinfarct dementia; amyotrophic lateral sclerosis; hypertension; tachycardia; congestive heart failure; osteoporosis; premature birth; and hypoglycemia in a mammal, comprising an amount of a compound according to claim 1 that is effective in the treatment of such disorder, and a pharmaceutically acceptable carrier.

18. A pharmaceutical composition, comprising a CRH binding protein inhibiting amount of a compound according to claim 1 and a pharmaceutically acceptable carrier.

19. A pharmaceutical composition according to claim 17 for the treatment of an inflammatory disorder selected from the group consisting of rhematoid arthritis and osteo arthritis.

20. A pharmaceutical composition according to claim 17 for treatment of fibromyalgia.

21. A pharmaceutical composition according to claim 17 for treatment of depression.

22. A pharmaceutical composition according to claim 21, wherein the depression is selected from the group consisting of major depression, single episode depression, recurrent depression, child abuse induced depression, and psotpartum depression.

23. A pharmaceutical composition according to claim 17 for treatment of mood disorders associated with premenstrual syndrome.

24. A pharmaceutical composition according to claim 17 for treatment of a neurogenerative disease selected from the group consisting of Alzheimer's disease, Parkinson's disease and Huntington's disease.

25. A pharmaceutical composition according to claim 17 for treatment of an eating disorder selected from the group consisting of anorexia and bulimia nervosa.

26. A method for the treatment of a disorder slected from inflammatory disorders, pain, asthma, psoriasis and allergies; generalized anxiety disorder; panic; phobias; obsessive-compulsive disorder; post-traumatic stress disorder; sleep disorders induced by stress; pain perception; mood disorders; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus (HIV) infections; neurodegenerative diseases; gastrointestinal diseases; eating disorders; hemorrhagic stress; chemical dependencies and addictions; drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage; excitotoxic neuronal damage; epilepsy; stroke; immune dysfunctions including stress induced immune dysfunctions; muscular spasms; urinary incontinence; senile dementia of the Alzheimer's type; multiinfarct dementia; amyotrophic lateral sclerosis; hypertension; tachycardia; congestive heart failure; osteoporosis; premature birth; and hypoglycemia in a mammal, comprising administering to a subject in need of said treatment an amount of a compound according to claim 1, that is effective in treating such disorder.

27. A method according to claim 26 wherein the compound is administered to the subject for treatment of an inflammatory disorder selected from the group consisting of rhematoid arthritis and osteo arthritis.

28. A method according to claim 26 wherein the compound is administered to the subject for treatment of fibromyalgia.

29. A method according to claim 26 wherein the compound is administered to the subject for treatment of depression.

30. A method according to claim 29, wherein the depression is selected from the group consisting of major depression, single episode depression, recurrent depression, child abuse induced depression, and psotpartum depression.

31. A method according to claim 26 wherein the compound is administered to the subject for treatment of mood disorders associated with premenstrual syndrome.

32. A method according to claim 26 wherein the compound is administered to the subject for treatment of a neurogenerative disease selected from the group consisting of Alzheimer's disease, Parkinson's disease and Huntington's disease.

33. A method according to claim 26 wherein the compound is administered to the subject for treatment of an eating disorder selected from the group consisting of anorexia and bulimia nervosa.

* * * * *

UNITED STATES PATENT AND TRADEMARK OFFICE
CERTIFICATE OF CORRECTION

PATENT NO. : 6,875,769 B2  Page 1 of 1
DATED : April 5, 2005
INVENTOR(S) : Yuhpyng L. Chen It is certified that error appears in the above-identified patent and that said Letters Patent is hereby corrected as shown below:

<u>Title page, Item [54] and Column 1, line 1,</u>
Title, "SUBSTITUTED6" should read -- SUBSTITUTED 6 --; and
Item [63], Related U.S. Application Data, delete "a continuation of" and "1997" should read -- 1997, which claims the benefit of U.S. Provisional Patent Application 60/018,198, filed on May 23, 1996 --.

Signed and Sealed this

Twenty-seventh Day of September, 2005

JON W. DUDAS
*Director of the United States Patent and Trademark Office*